US010722197B2

(12) United States Patent
Distler et al.

(10) Patent No.: US 10,722,197 B2
(45) Date of Patent: Jul. 28, 2020

(54) ARRANGEMENT WITH A STATIONARY PART AND A FIRST ROTATING PART OF A GANTRY OF A COMPUTED TOMOGRAPHY SCANNER AND METHOD FOR MAINTAINING A COMPONENT OF A GANTRY OF A COMPUTED TOMOGRAPHY SCANNER

(71) Applicant: Siemens Healthcare GmbH, Erlangen (DE)

(72) Inventors: Friedrich Distler, Fuerth (DE); Uli Holzermer, Erlangen (DE); Hans-juergen Mueller, Pretzfeld (DE); Christian Willming, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 507 days.

(21) Appl. No.: 15/440,307

(22) Filed: Feb. 23, 2017

(65) Prior Publication Data

US 2017/0258428 A1    Sep. 14, 2017

(30) Foreign Application Priority Data

Mar. 11, 2016  (DE) .......................... 10 2016 204 006

(51) Int. Cl.
*A61B 6/00* (2006.01)
*A61B 6/03* (2006.01)

(52) U.S. Cl.
CPC ............ *A61B 6/4447* (2013.01); *A61B 6/032* (2013.01); *A61B 6/035* (2013.01); *A61B 6/4488* (2013.01)

(58) Field of Classification Search
CPC ....... A61B 6/032; A61B 6/035; A61B 6/4447; A61B 6/4441
See application file for complete search history.

(56) References Cited

U.S. PATENT DOCUMENTS

2007/0092066 A1   4/2007  Laurentius
2007/0092068 A1*  4/2007  Albert .................... B66F 5/025
                                                       378/198
(Continued)

FOREIGN PATENT DOCUMENTS

CN    102843970 A    12/2012
CN    203576528 U     5/2014
(Continued)

OTHER PUBLICATIONS

German Office Action dated Dec. 20, 2017.
(Continued)

*Primary Examiner* — Dani Fox
(74) *Attorney, Agent, or Firm* — Harness, Dickey & Pierce, P.L.C.

(57) ABSTRACT

An arrangement includes a stationary part of a gantry of a computed tomography scanner and a first rotating part of the gantry of the computed tomography scanner. The first rotating part and the stationary part are connectable to one another via a bearing assembly such that the first rotating part is arranged in a bearing position relative to the stationary part and is mounted via the bearing assembly such that it is rotatable about a system axis. The first rotating part and the stationary part are connectable to one another via a holding apparatus such that the first rotating part is arranged in a holding position relative to the stationary part independently of the bearing assembly. In both the bearing position and the holding position, a central opening of the first rotating part and a central opening of the stationary part are arranged about the system axis.

33 Claims, 13 Drawing Sheets

(56) References Cited

U.S. PATENT DOCUMENTS

2013/0028389 A1    1/2013  Kalenyak et al.
2015/0110253 A1    4/2015  Distler et al.

FOREIGN PATENT DOCUMENTS

| CN | 104661421 A | 5/2015 |
|---|---|---|
| DE | 102005050634 A1 | 5/2007 |
| DE | 102008030833 A1 | 12/2009 |
| DE | 102013224886 A1 | 8/2015 |

OTHER PUBLICATIONS

Office Action for Chinese Patent Application No. 201710141798.5 dated May 12, 2020 and English translation thereof.
Office Action for Chinese Patent Application No. 201710141798.5 dated Dec. 26, 2019 and English translation thereof.

\* cited by examiner

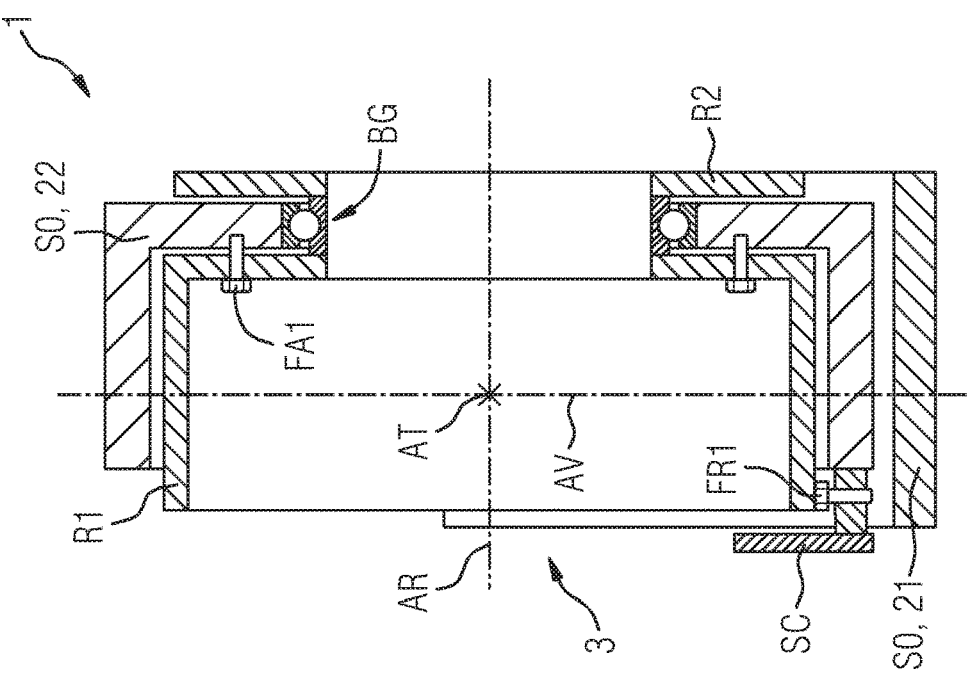
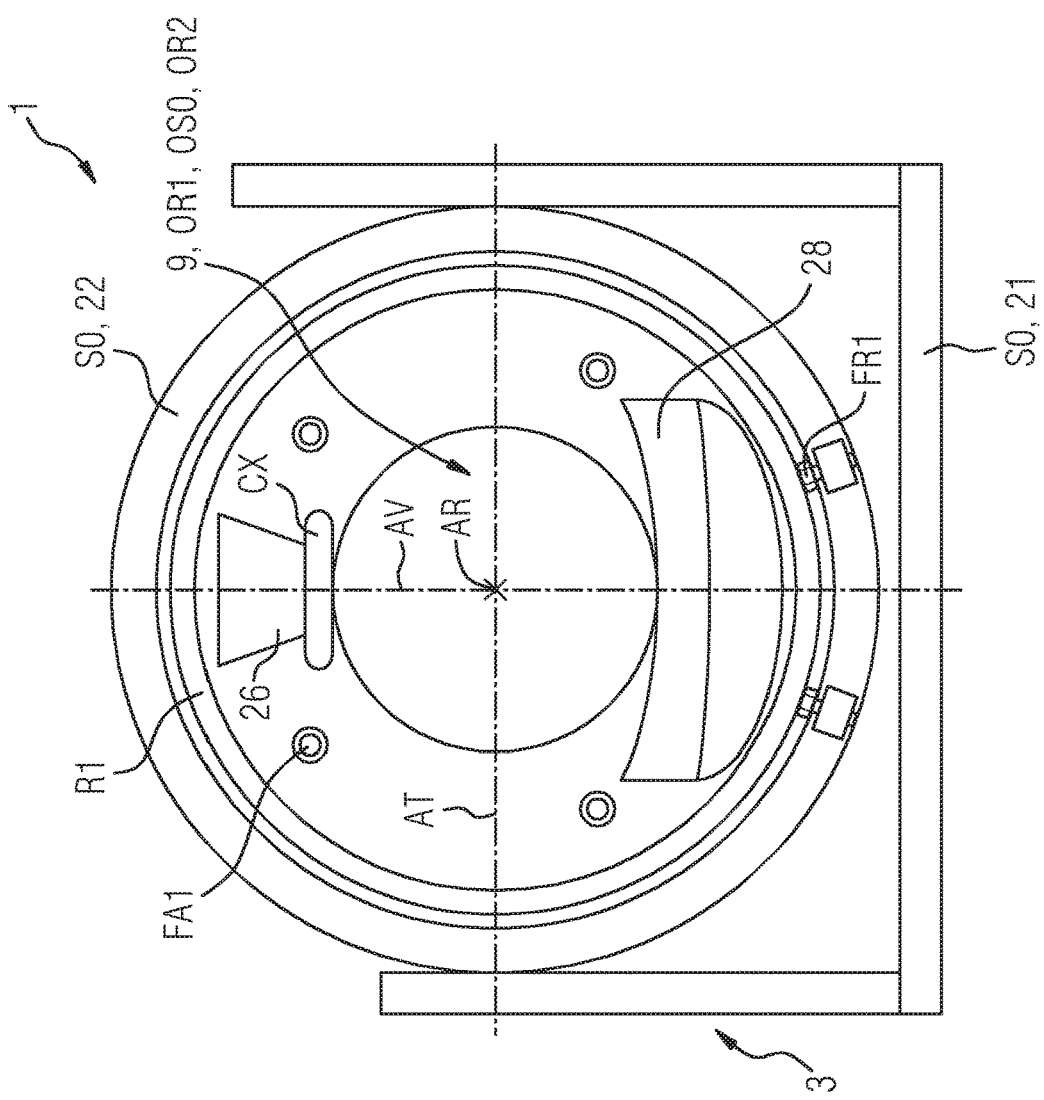

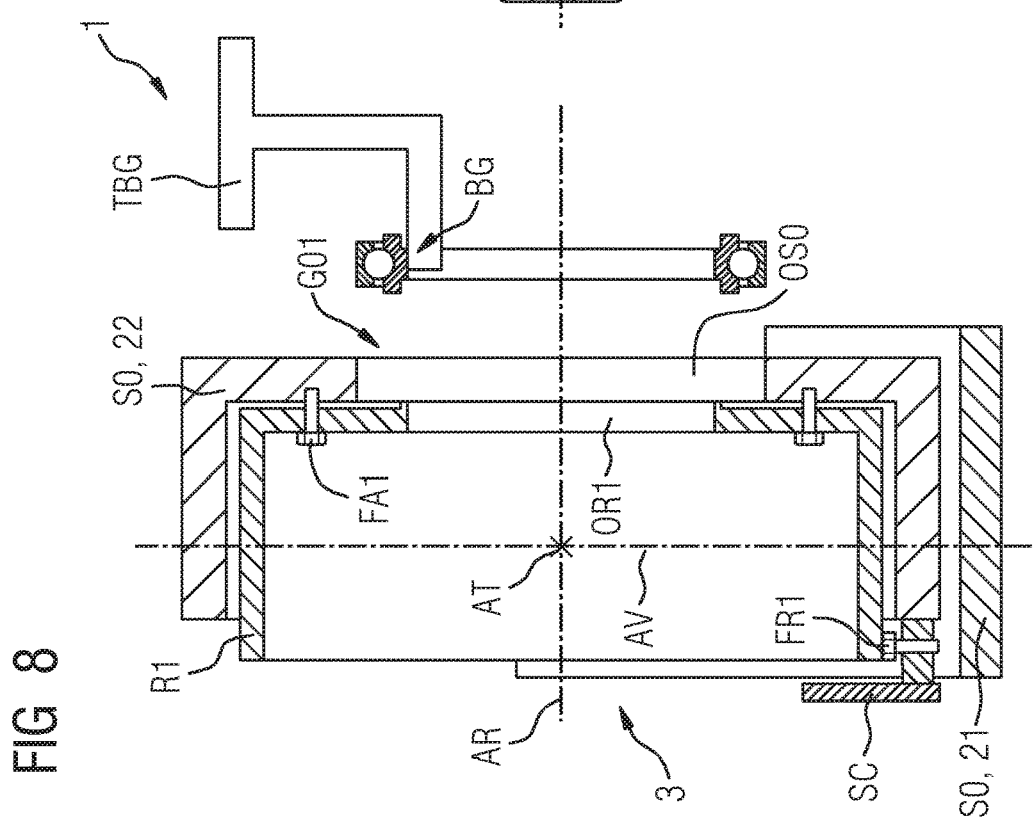

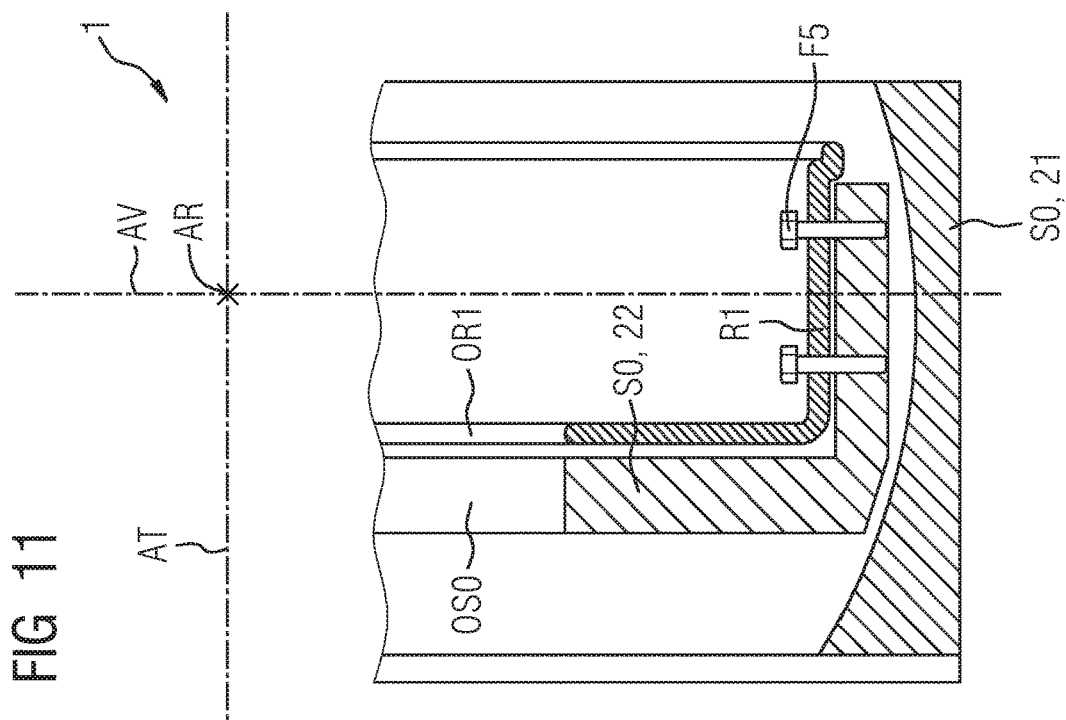
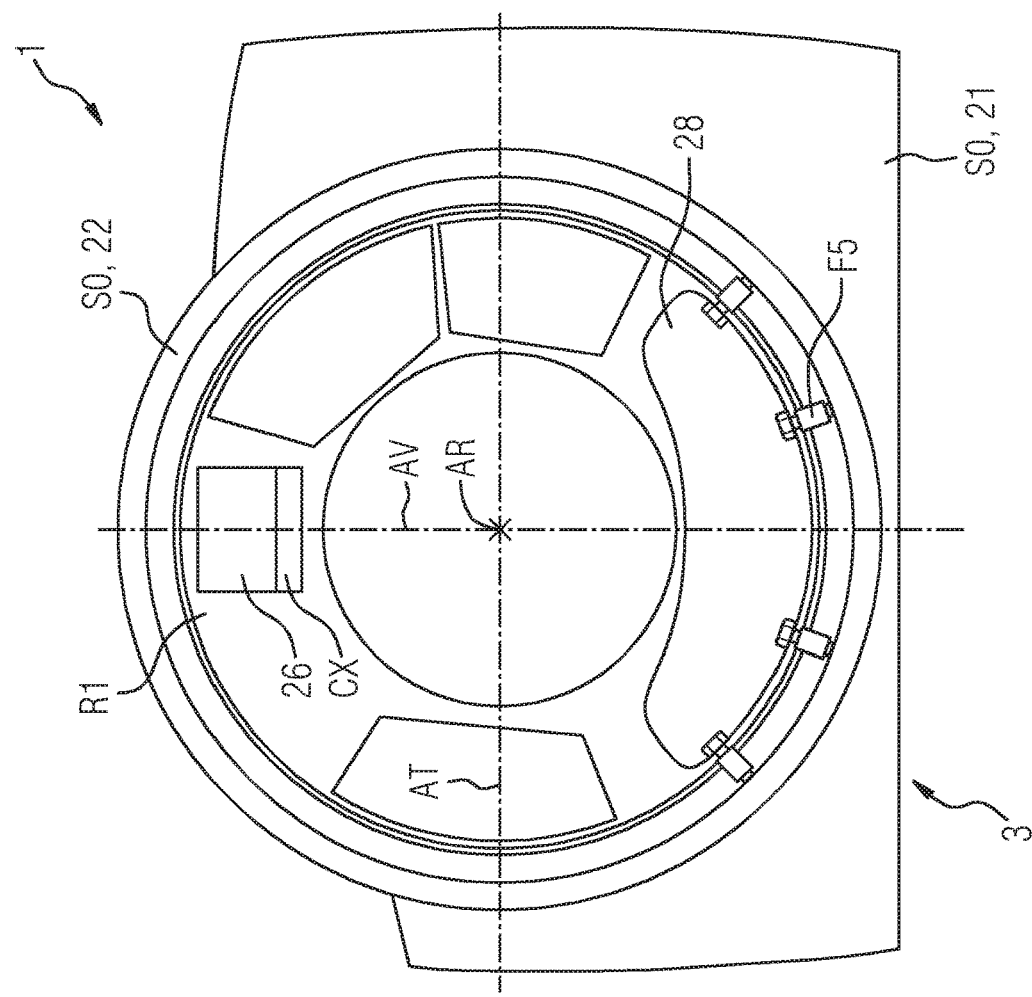

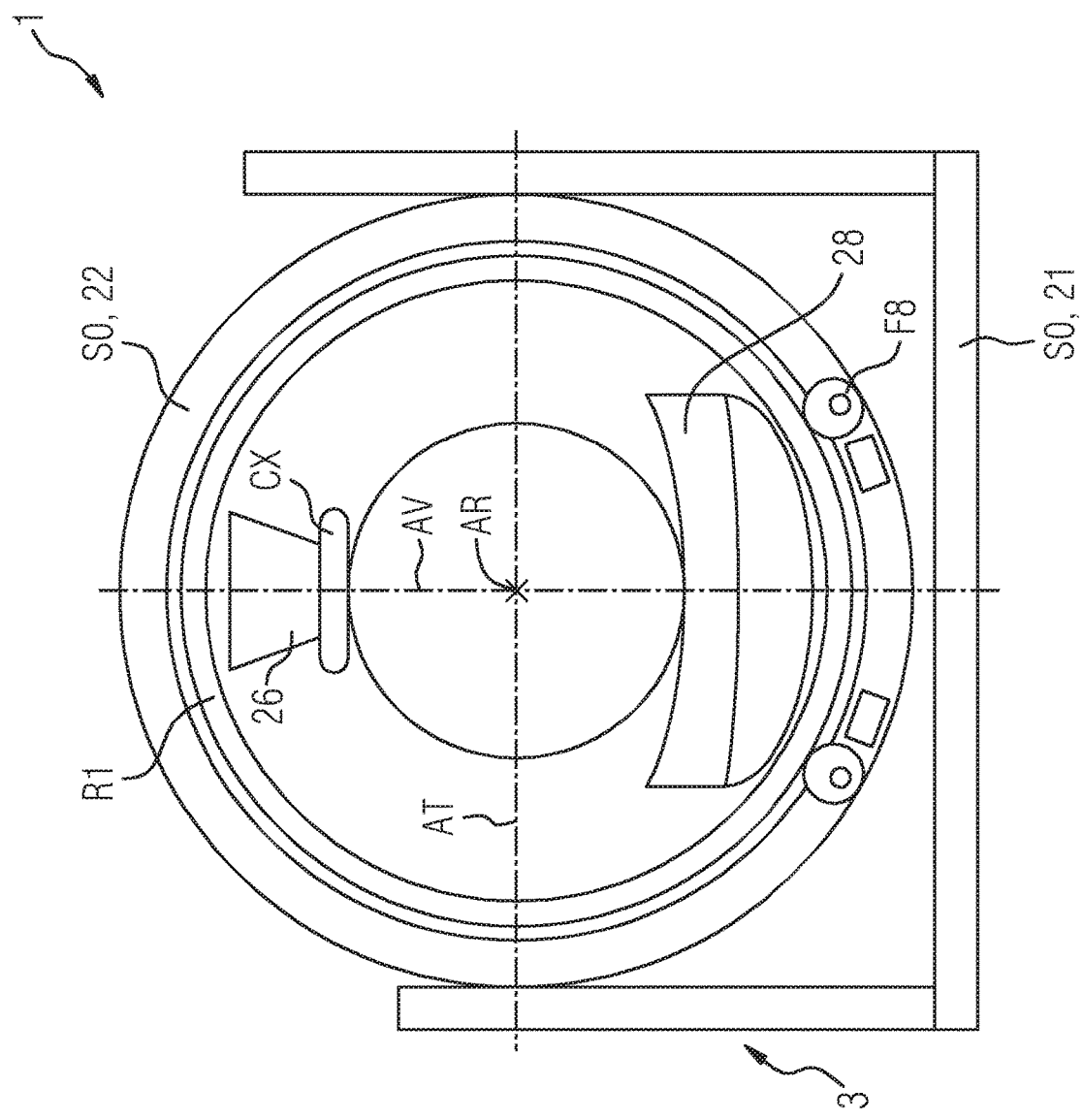

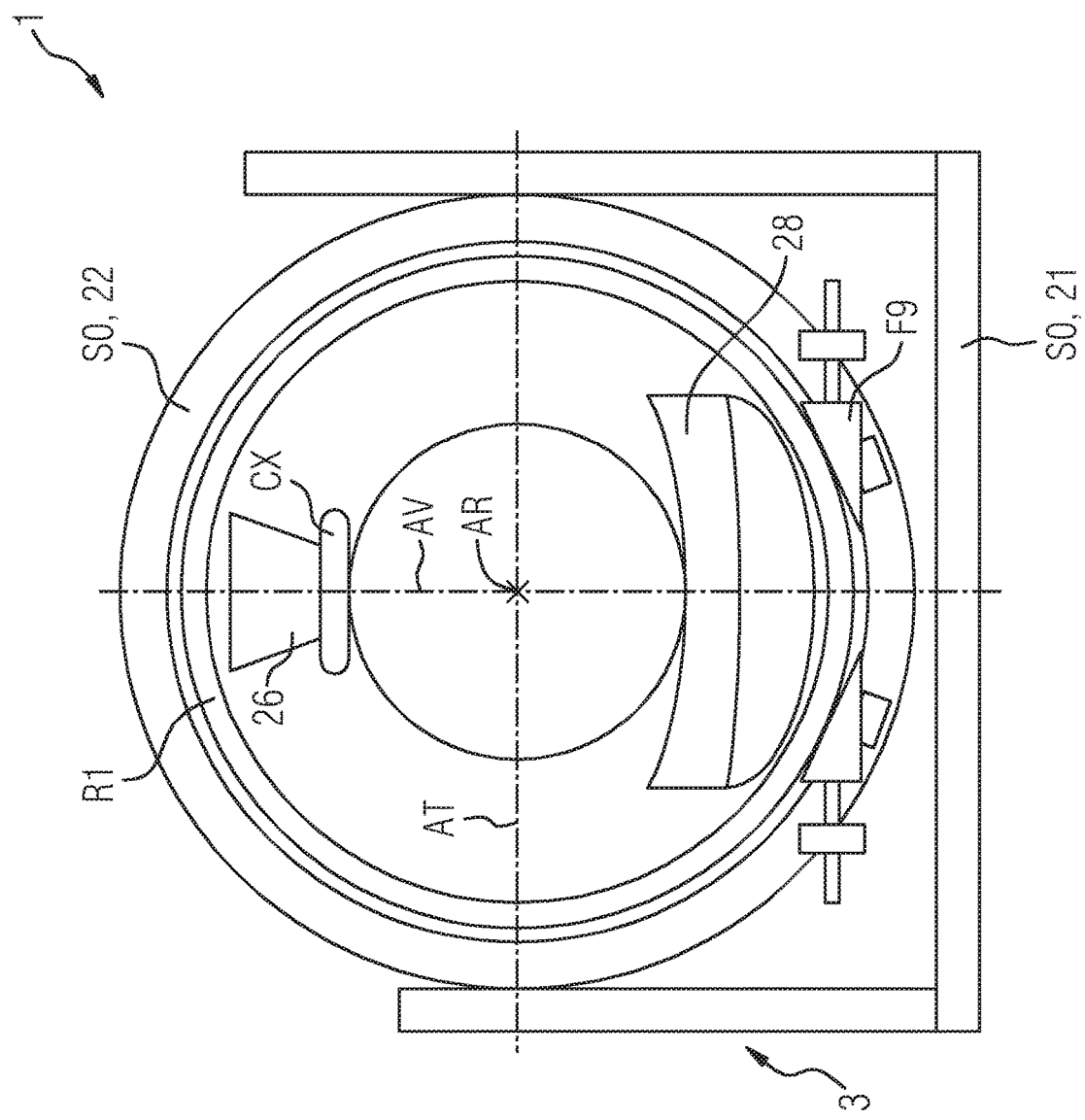

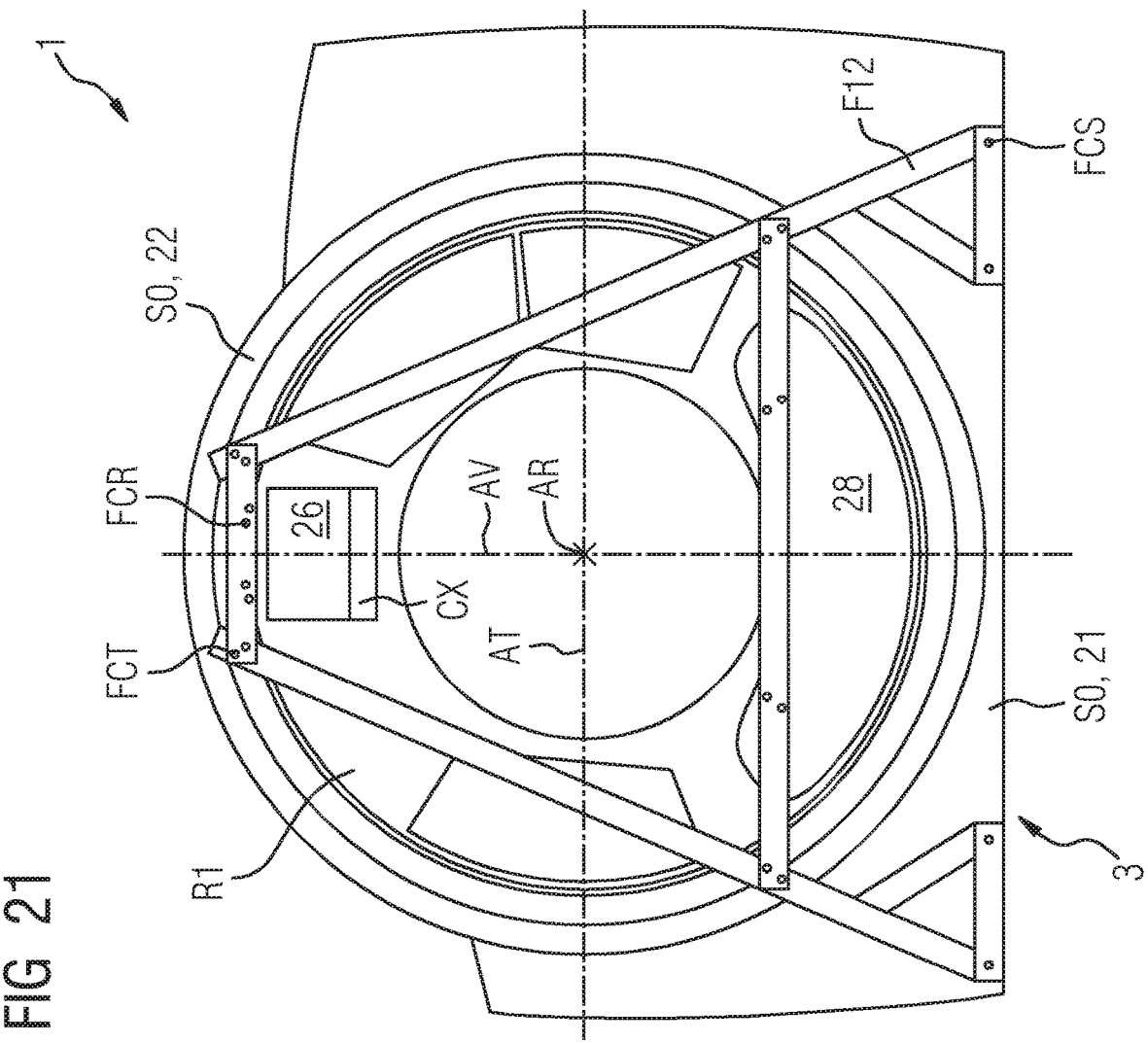

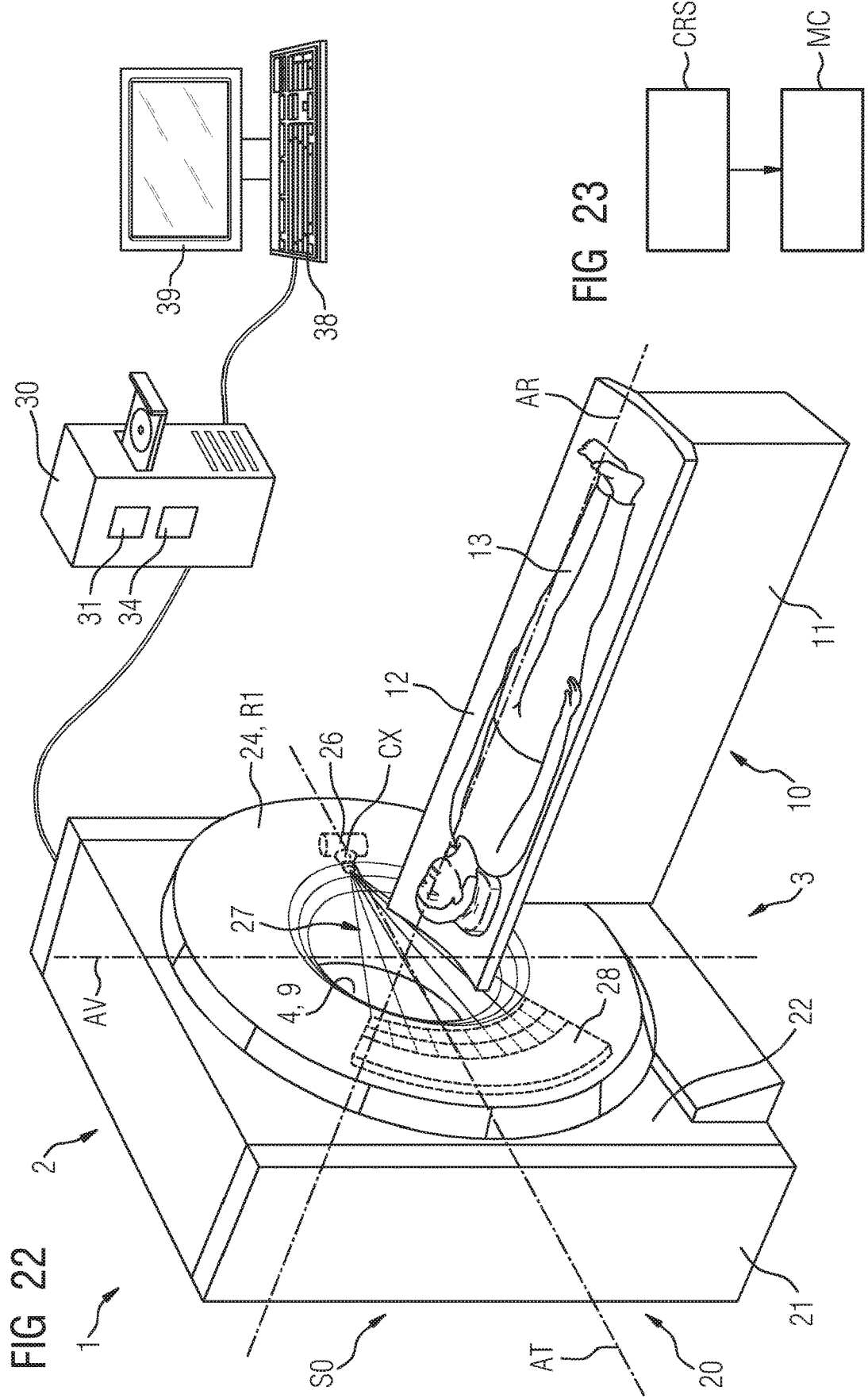

ARRANGEMENT WITH A STATIONARY PART AND A FIRST ROTATING PART OF A GANTRY OF A COMPUTED TOMOGRAPHY SCANNER AND METHOD FOR MAINTAINING A COMPONENT OF A GANTRY OF A COMPUTED TOMOGRAPHY SCANNER

PRIORITY STATEMENT

The present application hereby claims priority under 35 U.S.C. § 119 to German patent application number DE 102016204006.5 filed Mar. 11, 2016, the entire contents of which are hereby incorporated herein by reference.

FIELD

At least one embodiment of the invention generally relates to an arrangement with a stationary part of a gantry of a computed tomography scanner and a first rotating part of the gantry of the computed tomography scanner, wherein the first rotating part and the stationary part can be connected to one another via a bearing assembly such that that the first rotating part is arranged in a bearing position relative to the stationary part and is mounted such that it can be rotated about a system axis. At least one embodiment of the invention further relates to a method for maintaining a component of a gantry of a computed tomography scanner, wherein a first rotating part of the gantry and a first stationary part of the gantry can be connected to one another via a bearing assembly such that that the first rotating part is arranged in a bearing position relative to the first stationary part and mounted such that it can be rotated about a axis of rotation.

BACKGROUND

A computed tomography scanner typically comprises a bearing assembly for the rotatable mounting of a first rotating part, on which, for example, a radiation source and/or a radiation detector are arranged relative to a stationary part, which can, for example, comprise a supporting frame and/or a tilting frame. In order, for example in the case of damage to the bearing, to maintain, in particular replace and/or repair the bearing assembly, with conventional concepts, it is typically necessary to expose the bearing assembly in that the gantry is dismantled, wherein the first rotating part is separated from the stationary part and arranged separately from the stationary part. Alternatively, it is possible for a first gantry of which the bearing assembly is to be maintained to be replaced by a second gantry at the location of the computed tomography scanner, for example a medical examination room. This typically requires the stationary cabling of the first gantry to be dismantled. In the case of a fluid-cooled, in particular water-cooled, gantry, it may also be necessary to disconnect fluid-bearing parts and/or to empty cooling modules. The first gantry can then be transported to a factory where the bearing assembly is maintained with the infrastructure available there. Both procedures require a large amount of space and entail high expenditure in terms of time and costs. In particular, the dismantling of the gantry in situ and the subsequent reassembly and readjustment of the components of the computed tomography scanner relative to one another can be susceptible to errors.

SUMMARY

At least one embodiment of the invention enables improved maintenance of a component of a gantry of a computed tomography scanner.

At least one embodiment of the invention is directed to an arrangement and at least one embodiment of the invention is directed to a method.

The arrangement according to at least one embodiment of the invention comprises a stationary part of a gantry of a computed tomography scanner and a first rotating part of the gantry of the computed tomography scanner. The first rotating part and the stationary part can be connected to one another via a bearing assembly such that that the first rotating part is arranged in a bearing position relative to the stationary part and/or that the first rotating part is mounted relative to the stationary part via the bearing assembly such that it can be rotated about a system axis. The first rotating part and the stationary part can be connected to one another via a holding apparatus such that the first rotating part is arranged in a holding position relative to the stationary part independently of the bearing assembly. Both in the bearing position and in the holding position, a central opening of the first rotating part and a central opening of the stationary part are arranged about the system axis.

The method for maintaining a component of a gantry of a computed tomography scanner according to an embodiment of the invention provides that a first rotating part of the gantry and a stationary part of the gantry can be connected to one another via a bearing assembly such that that the first rotating part is arranged in a bearing position relative to the stationary part and that the first rotating part is mounted via the bearing assembly relative to the stationary part such that it can be rotated about a system axis.

The method according to an embodiment of the invention comprises:
 connecting the first rotating part and the stationary part via holding apparatus such that the first rotating part is arranged in a holding position relative to the stationary part independently of the bearing assembly, wherein, in the holding position, a central opening of the first rotating part and a central opening of the stationary part are arranged about the system axis, and
 maintenance of the component of the gantry.

BRIEF DESCRIPTION OF THE DRAWINGS

The invention is described again below in more detail with reference to the attached figures and example embodiments. The representations in the figures are schematic representations and greatly simplified and not necessarily true to scale. In the context of this application, a term provided with a reference characters can be understood to mean an example embodiment for an identical term that has not been given a reference character. If different reference characters are used for one term, this can in particular relate to different example embodiments for this term.

The figures show.

DETAILED DESCRIPTION OF THE EXAMPLE EMBODIMENTS

Figure 1:
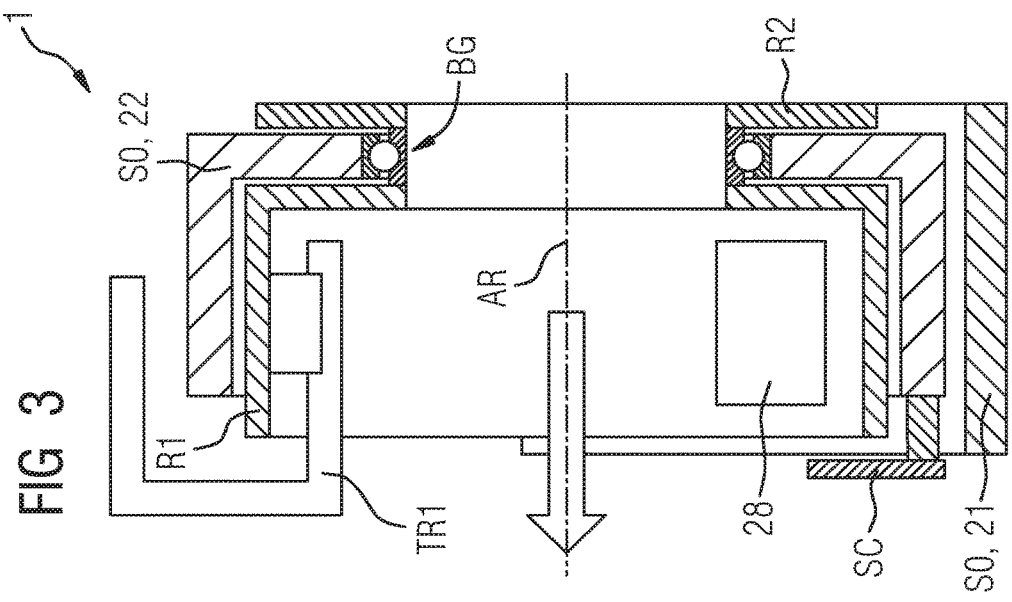
FIG. 1 a schematic representation of a gantry of a computed tomography scanner.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The arrangement according to at least one embodiment of the invention comprises a stationary part of a gantry of a computed tomography scanner and a first rotating part of the gantry of the computed tomography scanner. The first rotating part and the stationary part can be connected to one another via a bearing assembly such that that the first rotating part is arranged in a bearing position relative to the stationary part and/or that the first rotating part is mounted relative to the stationary part via the bearing assembly such that it can be rotated about a system axis. The first rotating part and the stationary part can be connected to one another via a holding apparatus such that the first rotating part is arranged in a holding position relative to the stationary part independently of the bearing assembly. Both in the bearing position and in the holding position, a central opening of the first rotating part and a central opening of the stationary part are arranged about the system axis.

According to one embodiment of the invention, the computed tomography scanner comprises an imaging-data acquisition unit embodied for the acquisition of imaging data. In particular, the imaging data-acquisition unit comprises a radiation source and a radiation detector.

One embodiment of the invention provides that the radiation source is embodied for the emission and/or excitation of radiation, in particular electromagnetic radiation, and/or that the radiation detector is embodied for the detection of radiation, in particular electromagnetic radiation. The radiation can, for example, travel from the radiation source to a region to be imaged and/or, following interaction with the region to be imaged, travel to the radiation detector. On interaction with the region to be imaged, the radiation is modified and becomes a carrier of information relating to the region to be imaged. On the interaction of the radiation with the detector, this information is captured in the form of the imaging data. With the computed tomography scanner, the imaging data projection data can be projection data, the imaging-data acquisition unit can be a projection data-acquisition unit, the radiation source can be an X-ray source and the radiation detector can be an X-ray detector. The X-ray detector can in particular be a quantum-counting and/or energy-resolving X-ray detector.

The computed tomography scanner can in particular be part of a combination of the computed tomography scanner with a further imaging modality and/or with an irradiation modality. According to one embodiment of the invention, the further imaging modality is selected from the imaging modality group consisting of an X-ray device, a C-arm X-ray device, a single-photon emission computed tomography scanner (SPECT device), a positron-emission tomography device (PET device), a magnetic resonance imaging device (MRI device) and combinations thereof. In this context, the irradiation modality can, for example, comprise an irradiation unit for therapeutic irradiation.

The computed tomography scanner comprises the gantry. The gantry comprises the stationary part of the gantry, the bearing assembly and the first rotating part of the gantry. In at least one functional operating state of the gantry, the first rotating part and the stationary part are connected to one another via the bearing assembly such that the first rotating part is mounted rotatably in a bearing position relative to the stationary part. In the functional operating state of the gantry, a tunnel-shaped opening and/or a lining of the tunnel-shaped opening extends substantially parallel to the system axis through the central opening of the first rotating part and through the central opening of the stationary part. A lining of the tunnel-shaped opening can in particular be understood to be a part of the lining of the gantry delimiting the tunnel-shaped opening and/or separating the tunnel-shaped opening from an internal region of the gantry.

A patient can be introduced into the tunnel-shaped opening. An acquisition region is located in the tunnel-shaped opening. A region to be imaged of the patient can be positioned in the acquisition region such that the radiation can travel from the radiation source to the region to be imaged and, following interaction with the region, can travel to the radiation detector. The central opening of the first rotating part is in particular arranged about the system axis when the system axis penetrates the central opening of the first rotating part. The central opening of the stationary part is in particular arranged about the system axis when the system axis penetrates the central opening of the stationary part.

According to one embodiment of the invention, the holding position can be offset relative to the bearing position such that, in the holding position, the system axis penetrates a different point of the central opening of the first rotating part than when in the bearing position.

According to one embodiment of the invention, the bearing assembly comprises a rotating bearing part, a stationary bearing part and a bearing. The rotating bearing part is connected to the first rotating part for common rotation with the first rotating part. The stationary bearing part is arranged fixed on the stationary part. In the context of this application, common rotation should in particular be understood to mean common rotation about the system axis.

According to one embodiment of the invention, the bearing is a rolling bearing. The rolling bearing comprises bearing rings with raceways, rolling elements, for example in the form of balls, and/or a rolling element cage. The rolling bearing is embodied for rolling the rolling elements on the raceways. The rolling bearing can, for example, be a barrel-shaped bearing, a ball bearing, an angular-contact ball bearing, a double-row angular-contact ball bearing or the like.

According to a further embodiment of the invention, alternatively and/or additionally to the rolling bearing, the bearing assembly comprises a fluid bearing and/or a magnet bearing.

The system axis coincides with the axis of rotation of the bearing assembly and/or of the first rotating part in the at least one functional operating state of the gantry in which the first rotating part and the stationary part are connected to one another via the bearing assembly such that the first rotating part is mounted rotatably in the bearing position relative to the stationary part. In particular, in an operating state of the arrangement in which the first rotating part and the stationary part are not connected to one another via the bearing assembly, this enables the position of the system axis to be defined relative to the stationary part of the gantry. According to one embodiment of the invention, the system axis is horizontal and/or substantially horizontal.

The holding apparatus is embodied for connecting the first rotating part and the stationary part according to one of the embodiments described in this application. In particular, the first rotating part and the stationary part can be connected to one another via the holding apparatus such that the first rotating part is arranged in the holding position relative to the stationary part independently of the bearing assembly, wherein the first rotating part is fixed relative to the stationary part via the holding apparatus and/or wherein the holding apparatus prevents a rotational movement of the first rotating part relative to the stationary part about the system axis. In particular, the first rotating part and the stationary part can be connected to one another via the holding apparatus such that the first rotating part is arranged in the holding position relative to the stationary part independently of the bearing assembly, wherein the holding apparatus prevents a translatory movement of the first rotating part relative to the stationary part along the system axis and/or a translatory movement of the first rotating part relative to the stationary part perpendicular to the system axis in each case in at least one direction and/or in two opposite directions. In particular, the first rotating part and the stationary part can be connected to one another via the holding apparatus such that the first rotating part is arranged in the holding position relative to the stationary part independently of the bearing assembly, wherein the holding apparatus is located inside a region defined by the outer circumference of the gantry. This enables a particularly space-saving arrangement to be achieved.

In particular, the first rotating part and the stationary part can be connected to one another via the holding apparatus starting from the bearing position such that the first rotating part is arranged in a holding position relative to the stationary part independently of the bearing assembly.

In the context of this application, the first rotating part should be understood to be the first rotating part of the gantry, the second rotating part to be the second rotating part of the gantry and the stationary part to be the stationary part of the gantry. In the context of this application, the holding position should be understood to be the holding position of the first rotating part relative to the stationary part and the bearing position to be the bearing position of the first rotating part relative to the stationary part.

The fact that the first rotating part is arranged in a holding position relative to the stationary part independently of the bearing assembly relieves the load on the bearing assembly. Hence, at least one embodiment of the invention enables improved maintenance of the bearing assembly.

At least one embodiment of the invention also enables improved maintenance in particular of components of the gantry during the maintenance of which forces and/or torques are generated that are transmitted from the first rotating part and/or from the second rotating part to the stationary part. Relieving the load on the bearing assembly via the holding apparatus protects the bearing assembly from these forces and/or torques.

At least one embodiment of the invention also enables improved maintenance in particular of components of the gantry during the maintenance of which forces and/or torques are generated that cannot be transmitted via the bearing assembly, for example because this effects a rotation of the first rotating part about the system axis.

At least one embodiment of the invention also enables simplified removal of the bearing assembly and hence improved maintenance in particular of those components of the gantry, which are covered by the bearing assembly. The component to be maintained can, for example, be the bearing assembly, the radiation source, the radiation detector, the second rotating part, the rotor-side data-transfer unit, the rotor-side power-transfer unit or the like. In particular during the maintenance of a component which is not the bearing assembly it can be advisable in some circumstances for the load on the bearing assembly to be only partly relieved via the holding apparatus and/or for the forces and/or torques generated during the maintenance to be transmitted partially via the bearing assembly and partially via the holding apparatus.

The solution according to at least one embodiment of the invention in particular renders the dismantling of the gantry, wherein the first rotating part is separated from the stationary part and arranged separately from the stationary part, unnecessary. In particular, it is not necessary for stationary cabling of the gantry to be uninstalled. In the case of a fluid-cooled gantry, no additional measures, in particular the emptying of cooling modules, are necessary. The solution according to the invention renders external lifting tackle and/or cranes unnecessary, in particular heavy lift cranes, for loading the first rotating part. Hence, essential parts of the gantry, in particular the first rotating part and the stationary part, can remain for the maintenance without any significant increase in the space requirement and/or without any significant change of position at the location of the computed tomography scanner, for example in a medical examination room.

In particular, no structural measures, for example widening of door openings, stabilization of false floors, are required. The transportation of the bearing assembly and/or components requiring maintenance, which are much lighter than the gantry, can be achieved with a lower expenditure in terms of time, logistics costs and infrastructure.

In particular, due to the low space requirement, the solution according to at least one embodiment of the invention does not require the position of a patient-bearing apparatus relative to the gantry, in particular relative to the stationary part, to be changed to facilitate maintenance. Hence, the patient-bearing apparatus does not have to be re-adjusted relative to the gantry following the maintenance. Special adjustment of the components, in particular the components arranged on the first rotating part for common rotation with the first rotating part, for example the radiation source and/or the radiation detector, following the maintenance is also not necessary with the solution according to at least one embodiment of the invention.

The solution according to at least one embodiment of the invention enables the maintenance of a component of the gantry, in particular of the bearing assembly, to be achieved with a lower space requirement, with lower expenditure in terms of time and costs and with a lower susceptibility to errors.

Alternatively and/or additionally to the fact that, in both the bearing position and the holding position, a central opening of the first rotating part and a central opening of the stationary part are arranged about the system axis, it can be provided that the holding position and the bearing position are arranged coaxially with respect to the system axis and/or that the holding position and the bearing position coincide with respect to the position along the system axis. The holding position and the bearing position can in particular be arranged coaxially with respect to the system axis when the holding position and the bearing position differ with respect to a position along the system axis, i.e. are offset with respect to another along the system axis. The holding position and the bearing position can in particular coincide with respect to the position along the system axis when the holding position and the bearing position differ with respect to a position along a direction perpendicular to the system axis, i.e. are offset with respect to one another along a direction perpendicular to the system axis.

Alternatively and/or additionally to the fact that, in both the bearing position and the holding position, a central opening of the first rotating part and a central opening of the stationary part are arranged about the system axis, it can be provided that the holding position and the bearing position are identical.

In particular, this discloses an arrangement comprising a stationary part of a gantry of a computed tomography scanner and a first rotating part of the gantry of the computed tomography scanner, wherein the first rotating part and the stationary part can be connected to one another via a bearing assembly such that the first rotating part is arranged in a bearing position relative to the stationary part and is mounted via the bearing assembly such that it can be rotated about a system axis, wherein the first rotating part and the stationary part can be connected to one another via a holding apparatus such that the first rotating part is arranged in the bearing position relative to the stationary part independently of the bearing assembly. This arrangement can be developed according to one of the embodiments of the invention described in this application.

According to one embodiment of the invention, it is provided that the arrangement is embodied to adopt a first operating state of the arrangement and/or that the arrangement is in the first operating state of the arrangement. In the first operating state of the arrangement, the first rotating part and the stationary part are connected to one another via the holding apparatus such that the first rotating part is arranged in the holding position relative to the stationary part independently of the bearing assembly.

According to one further embodiment of the invention, in the first operating state of the arrangement, a connection between the bearing assembly and the first rotating part, in particular the rotor-side connecting apparatus, and/or a connection between the bearing assembly and the stationary part, in particular the stator-side connecting apparatus, can be established and/or disconnected.

According to one embodiment of the invention, in the first operating state of the arrangement, a connection between the bearing assembly and a support apparatus for supporting the bearing assembly can be established and/or disconnected. The support apparatus can for example be a crane. The support apparatus can in particular be a gantry crane and/or a mobile crane. The crane can in particular be matched to the bearing assembly and/or be relatively small compared to a crane embodied to load the first rotating part.

According to one embodiment of the invention, in the first operating state of the arrangement, the bearing assembly can be received in an interspace parallel to the system axis and/or removed from the interspace parallel to the system axis. According to one further embodiment of the invention, in the first operating state of the arrangement, the bearing assembly can be received in an interspace via the support apparatus parallel to the system axis and/or removed from the interspace via the support apparatus parallel to the system axis. The interspace is embodied between the first rotating part and the stationary part to receive the bearing assembly in particular such that the first rotating part and the stationary part can be connected to one another via a bearing assembly located in the interspace such that the first rotating part is arranged in the bearing position relative to the stationary part and is mounted rotatably about the system axis embodiment the bearing assembly.

According to one embodiment of the invention, the arrangement further comprises at least one apparatus selected from the group consisting of the bearing assembly, the holding apparatus, the support apparatus, the gantry, the computed tomography scanner and combinations thereof.

In particular, the arrangement can comprise the bearing assembly and/or the holding apparatus. In particular, the arrangement can comprise the support apparatus. In particular, the arrangement can comprise the gantry and/or the computed tomography scanner.

According to one embodiment of the invention, it is provided that the stationary part comprises a tilting frame of the gantry and/or a supporting frame of the gantry and/or that the tilting frame is mounted relative to the supporting frame so that it can be tilted about a tilting axis.

According to one embodiment of the invention, the stationary part is a tilting frame of the gantry and/or a supporting frame of the gantry. According to one embodiment of the invention, the stationary part is a combination of a tilting frame of the gantry with a supporting frame of the gantry. The supporting frame is typically arranged fixed relative to a support, for example a base and/or a baseplate, and/or relative to a patient-bearing apparatus. In particular, if the bearing assembly is arranged on the tilting frame, the system axis can be inclined relative to a horizontal plane. In particular, the tilting frame can be mounted relative to the supporting frame via a tilting bearing so that it can be tilted about a tilting axis. In particular, the tilt axis can be perpendicular and/or substantially perpendicular to the system axis. In particular, the tilt axis can be horizontal. This enables an inclination of the system axis relative to a horizontal plane to be set via the tilting bearing. One embodiment of the invention provides that the system axis is horizontal and/or that the system axis is horizontal in the first operating state of the arrangement.

According to one embodiment of the invention, it is provided that the first rotating part is embodied to receive a radiation source and/or a radiation detector. According to one embodiment of the invention, the radiation source and/or the radiation detector is arranged on the first rotating part for common rotation with the first rotating part.

According to one embodiment of the invention, the arrangement further comprises a second rotating part of the gantry. According to one embodiment of the invention, the arrangement can adopt a second operating state of the arrangement. In the second operating state of the arrangement, the second rotating part is arranged on the bearing assembly and/or on the first rotating part for common rotation with the first rotating part such that the bearing assembly is located between the first rotating part and the second rotating part with respect to a direction parallel to the system axis.

According to one further embodiment of the invention, in the first operating state of the arrangement, the second rotating part is located at a distance from the bearing assembly and/or from the first rotating part such that the bearing assembly and/or the interspace is exposed on a side facing away from the first rotating part with respect to the direction parallel to the system axis, in particular exposed such that the bearing assembly can be received in an interspace parallel to the system axis and/or removed from the interspace parallel to the system axis.

According to one embodiment of the invention/arrangement, it is provided that the second rotating part is embodied:
to receive a rotor-side data-transfer unit of a data transfer apparatus embodied to transfer data between the second rotating part and the stationary part and/or
to receive a rotor-side power-transfer unit of a power-transfer apparatus embodied to transfer power between the second rotating part and the stationary part.

In particular, the rotor-side data-transfer unit and/or the rotor-side power-transfer unit can be arranged on the second rotating part.

According to one embodiment of the invention/arrangement, it is provided that the first rotating part is embodied:
to receive a rotor-side data-transfer unit of a data transfer apparatus embodied to transfer data between the first rotating part and the stationary part and/or
to receive a rotor-side power-transfer unit of a power-transfer apparatus embodied to transfer power between the first rotating part and the stationary part. In particular, the rotor-side data-transfer unit and/or the rotor-side power-transfer unit can be arranged on the first rotating part. The rotor-side data-transfer unit can in particular be connected to a component arranged on the first rotating part, for example to the radiation source and/or to the radiation detector, for the transmission of data, for example control data and/or imaging data, to the component and/or from the component. The rotor-side power-transfer unit can in particular be connected to a component arranged on the first rotating part, for example to the radiation source and/or to the radiation detector, for the transmission of power to the component.

According to a further embodiment of the invention, it is provided that, in particular in the functional operating state of the gantry, the second rotating part is arranged on the bearing assembly and/or on the first rotating part for common rotation with the first rotating part such that the second rotating part is located between the first rotating part and the bearing assembly with respect to a direction parallel to the system axis.

According to one embodiment, it is provided that, in particular in the functional operating state of the gantry, the bearing assembly and/or the interspace is exposed on a side facing away from the first rotating part with respect to a direction parallel to the system axis, in particular is exposed such that the bearing assembly can be received in an interspace parallel to the system axis and/or removed from the interspace parallel to the system axis.

In the context of this application, a given component is in particular on the rotor side when the given component is assigned to the first rotating part and/or the second rotating part. In the context of this application, a given component is in particular on the stator side when the given component is assigned to the stationary part. The data-transfer apparatus can, for example, be embodied for contact-free data transfer and/or for contacting data transfer between the second rotating part and the stationary part. The contacting data transfer can in particular take place via a slip ring. In particular, the second rotating part and/or the rotor-side data-transfer unit can comprise the slip ring.

According to one embodiment of the invention, it is provided that the holding apparatus is embodied to form a disconnectable and/or positive connection with the first rotating part, in particular with the rotor-side connecting apparatus, and/or to form a disconnectable and/or positive connection with the stationary part, in particular with the stator-side connecting apparatus.

According to one embodiment of the invention, it is provided that the first rotating part comprises at least one rotor-side connecting apparatus, which is embodied to form a disconnectable and/or positive connection with the holding apparatus, in particular is embodied such that the first rotating part, in particular the rotor-side connecting apparatus, and the stationary part, in particular the stator-side connecting apparatus, can be connected to one another via the holding apparatus such that the first rotating part is arranged in a holding position relative to the stationary part independently of the bearing assembly, wherein in both the bearing position and the holding position, a central opening of the first rotating part and a central opening of the stationary part are arranged about the system axis.

According to one further embodiment of the invention, it is provided that the stationary part comprises at least one stator-side connecting apparatus which is embodied to form a disconnectable and/or positive connection with the holding apparatus, in particular is embodied such that the first rotating part, in particular the rotor-side connecting apparatus, and the stationary part, in particular the stator-side connecting apparatus, can be connected to one another via the holding apparatus such that the first rotating part is arranged in a holding position relative to the stationary part independently of the bearing assembly, wherein in both the bearing position and the holding position, a central opening of the first rotating part and a central opening of the stationary part are arranged about the system axis.

Both the rotor-side connecting apparatus and the stator-side connecting apparatus can in each case comprise a connecting element or a plurality of connecting elements, which can, for example, be spatially separate from one another. The connecting element and/or each of the plurality of connecting elements can, for example, be selected from the connecting-element group consisting of a thread, a threaded insert, a coupling, a holder, a shoulder, a recess, a bearing surface, a support point and combinations thereof. In particular, the bearing surface can be flat and/or curved.

According to one embodiment of the invention, it is provided that the holding apparatus comprises an axial part of the holding apparatus, wherein the first rotating part and the stationary part can be connected to one another via the axial part of the holding apparatus such that the first rotating part is arranged in the holding position relative to the stationary part with respect to the position along the system axis independently of the bearing assembly. In particular, when a connection between the bearing assembly and the first rotating part is disconnected, the axial part of the holding apparatus is able to prevent a tilting movement of the first rotating part about a horizontal axis perpendicular to the system axis.

According to one embodiment of the invention, it is provided that the holding apparatus comprises a radial part of the holding apparatus, wherein the first rotating part and the stationary part can be connected to one another via the radial part of the holding apparatus such that the first rotating part is arranged independently of the bearing assembly in the holding position relative to the stationary part with respect to the position along a direction perpendicular to the system axis. This enables the load on the bearing assembly to be relieved in particular with respect to forces acting in a direction perpendicular to the system axis on the first rotating part and/or affected by the first rotating part.

According to one embodiment of the invention, it is provided that the holding apparatus is a holding element selected from the holding-element group or a plurality of holding elements each selected from the holding-element group. The holding-element group includes a screw, a threaded sleeve, a spacer sleeve, a bolt, a threaded bolt, an adjusting foot, a screwing apparatus, a supporting apparatus, a lifting apparatus, a jack, an aircushion, an eccentric apparatus, a wedge apparatus, a holding segment, a holding rack and combinations thereof.

In particular, the holding apparatus can comprise a plurality of different holding elements each selected from the holding-element group. The plurality of holding elements of the holding apparatus can in particular be spatially separate from one another. In particular, a holding element of the holding apparatus can be embodied to form a disconnectable and/or positive connection with a connecting element of the stator-side connecting apparatus and/or with a connecting element of the rotor-side connecting apparatus. The threaded sleeve can, for example, comprise an internal thread and/or an external thread. The jack can, for example, be a heavy-vehicle jack.

The method for maintaining a component of a gantry of a computed tomography scanner according to an embodiment of the invention provides that a first rotating part of the gantry and a stationary part of the gantry can be connected to one another via a bearing assembly such that that the first rotating part is arranged in a bearing position relative to the stationary part and that the first rotating part is mounted via the bearing assembly relative to the stationary part such that it can be rotated about a system axis.

The method according to an embodiment of the invention comprises:
  connecting the first rotating part and the stationary part via holding apparatus such that the first rotating part is arranged in a holding position relative to the stationary part independently of the bearing assembly, wherein, in the holding position, a central opening of the first rotating part and a central opening of the stationary part are arranged about the system axis, and
  maintenance of the component of the gantry.

According to one embodiment of the invention, it is provided that the maintenance of the component of the gantry comprises repairing the component of the gantry and/or replacing the component of the gantry.

According to one embodiment of the invention, it is provided that a connection between the bearing assembly and the first rotating part and/or a connection between the bearing assembly and the stationary part is established and/or disconnected.

According to one embodiment of the invention, it is provided that a connection between the bearing assembly and a support apparatus for supporting the bearing assembly is established and/or disconnected.

According to one embodiment of the invention, it is provided that the bearing assembly is received in an interspace embodied between the first rotating part and the stationary part to receive the bearing assembly parallel to the system axis and/or removed from the interspace parallel to the system axis.

According to one embodiment of the invention, it is provided that a second rotating part is located at a distance from the bearing assembly and/or from the first rotating part such that the bearing assembly and/or the interspace is exposed on a side facing away from the first rotating part with respect to a direction parallel to the system axis, in particular is exposed such that the bearing assembly can be received in an interspace parallel to the system axis and/or removed from the interspace parallel to the system axis.

According to one further embodiment of the invention, it is provided that the second rotating part is arranged on the bearing assembly and/or on the first rotating part for common rotation with the first rotating part, in particular arranged such that the bearing assembly is located between the first rotating part and the second rotating part with respect to the direction parallel to the system axis.

According to one embodiment of the invention, it is provided that the component of the gantry is the bearing assembly and/or that the component of the gantry is arranged on at least one mechanism selected from the group consisting of the bearing assembly, the first rotating part, the stationary part and combinations thereof.

According to one embodiment of the invention, it is provided that a second rotating part is arranged on the bearing assembly and/or on the first rotating part for common rotation with the first rotating part and that the component of the gantry is the second rotating part and/or arranged on the second rotating part.

According to one embodiment of the invention, it is provided that the method according to the invention is carried out according to one of the embodiments described in this application with an arrangement according to one of the embodiments described in this application.

Within the context of at least one embodiment of the invention, features described with respect to different embodiments of the invention and/or different claim categories (apparatus, method etc) can be combined to form further embodiments of the invention. In other words, the substantive claims can also be developed with the features described or claimed in connection with a method. Functional features of a method according to the method can also be carried out by way of correspondingly embodied substantive components. In addition to the embodiments of the invention expressly described in this application, numerous further embodiments of the invention are conceivable which the person skilled in the art will be able to arrive at without departing from the scope of the invention as defined in the claims.

The use of indefinite article "a" or "an" does not preclude the possibility of the features in question also being present on a multiple basis. The use of the expression "comprise" does not preclude the possibility of the terms being linked by the expression "comprise" being identical. For example, the medical imaging apparatus comprises the medical imaging apparatus. The use of the expression "unit" does not preclude the possibility of the subject matter to which the expression "unit" relates comprising a plurality of components that are spatially separated from one another. In the context of the present application, the use of ordinal numbers (first, second, third etc.) in the description of features is primarily for better distinction of those features described using ordinal numbers. The absence of a feature described by a combination of a given ordinal number and a term does not preclude the possibility of a feature being present that is also described by a combination of an ordinal number following the given ordinal number and the term. Furthermore, the possibility is not precluded that, during the performance of a method according to one of the embodiments described in this application, a feature described by a combination of a given ordinal number and a term, for example a second operating state with respect to the temporal sequence, is performed earlier than a feature described by a combination of an ordinal number preceding the given ordinal number and the term, for example a first operating state.

In the context of the present application, the expression "based on" can in particular be understand as meaning "using". In particular, wording according to which a first feature is created (alternatively: determined, identified etc.) based on a second feature does not preclude the possibility of the first feature being created (alternatively: determined, identified etc.) based on a third feature.

FIG. 1 is a schematic representation of a gantry 20 of a computed tomography scanner 2. The gantry 20 comprises the stationary part S0 of the gantry 20, the bearing assembly BG, the first rotating part R1 and the second rotating part R2. In FIG. 1, the gantry 20 is shown in the at least one functional operating state of the gantry 20. The first rotating part R1 and the stationary part S0 are connected to one another via the bearing assembly BG such that the first rotating part R1 is mounted rotatably about the system axis AR in a bearing position relative to the stationary part S0. The central opening OR1 of the first rotating part R1 and the central opening OS0 of the stationary part S0 are arranged about the system axis AR. In the functional operating state of the gantry 20, the tunnel-shaped opening 9 and/or a lining of the tunnel-shaped opening 9 extends substantially parallel to the system axis AR through the central opening OR1 of the first rotating part R1 and through the central opening OS0 of the stationary part S0. Furthermore, in the functional operating state of the gantry 20, the tunnel-shaped opening 9 and/or the lining of the tunnel-shaped opening 9 extends substantially parallel to the system axis AR through the central opening OR2 of the second rotating part R2. The first rotating part R1 comprises a rotor wall R1D, which substantially has the shape of a first ring wheel, and a holding ring R1M. The holding ring R1M substantially has the shape of a cylindrical jacket and is arranged encircling the outer circumference of the rotor wall R1D. The holding ring R1M is embodied to receive components of the gantry 20, in particular the radiation source 26, the radiation detector 28 and the collimator CX. The rotor wall R1D and the holding ring R1M together form a drum-shaped frame, which is also known to the person skilled in the art by the term "drum". The first rotating part R1 comprises the drum-shaped frame.

The second rotating part R2 is arranged on the bearing assembly BG for common rotation with the first rotating part R1 such that the bearing assembly BG is located between the first rotating part R1 and the second rotating part R2 with respect to the system axis AR. The rotor-side data-transfer unit and the rotor-side power-transfer unit are arranged on the second rotating part R2.

The stationary part S0 is a combination of a tilting frame 22 of the gantry 20 with a supporting frame 21 of the gantry 20. The tilt axis AT is perpendicular and/or substantially perpendicular to the system axis AR. The tilt axis AT is perpendicular and/or substantially perpendicular to the vertical axis AV. The tilt axis AT is horizontal. FIGS. 4 to 21 each shown an operating state of the arrangement 1 in which the system axis AR is horizontal.

Figure 2:
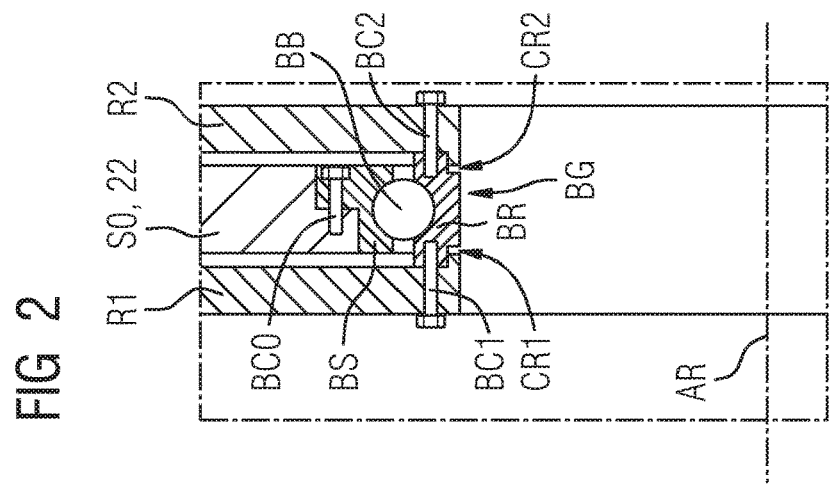
FIG. 2 a schematic representation a bearing assembly.

FIG. 2 is a schematic representation of the bearing assembly BG. The bearing assembly BG comprises a rotating bearing part BR, a stationary bearing part BS and a bearing BB, for example a rolling bearing. The rotating bearing part BR is connected via the connection BC1 to the first rotating part R1 for common rotation with the first rotating part R1. The rotating bearing part BR is connected via the connection BC2 to the second rotating part R2 for common rotation with the second rotating part R2. The stationary bearing part BS is arranged fixed on the stationary part S0 and connected via the connection BC0 to the stationary part S0. The connections BC0, BC1 and BC2 are in each case screwed connections arranged axially, in particular parallel, to the system axis AR with respect to the system axis AR.

In the region of the connection of the first rotating part R1 to the rotating bearing part BR, the first rotating part R1 comprises a shoulder. In the region of the connection of the first rotating part R1 to the rotating bearing part BR, the rotating bearing part BR comprises a recess corresponding to the shoulder of the first rotating part R1. The shoulder of the first rotating part R1 and the recess of the rotating bearing part BR corresponding thereto together form a centering apparatus CR1 for centering the first rotating part R1 relative to the rotating bearing part BR.

In the region of the connection of the second rotating part R2 to the rotating bearing part BR, the second rotating part R2 comprises a shoulder. In the region of the connection of the second rotating part R2 to the rotating bearing part BR, the rotating bearing part BR comprises a recess corresponding to the shoulder of the second rotating part R2. The shoulder of the second rotating part R2 and the recess of the rotating bearing part BR corresponding thereto together form a centering apparatus CR2 for centering the second rotating part R2 relative to the rotating bearing part BR.

Figure 3:
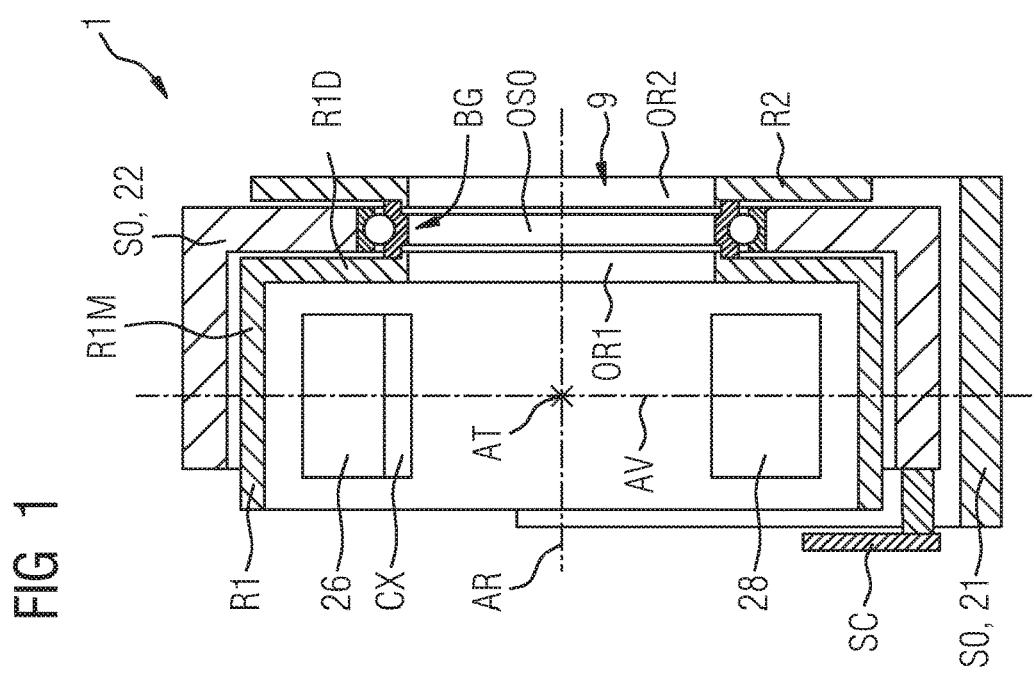
FIG. 3 a schematic representation of a gantry of a computed tomography scanner and a crane apparatus, FIG. 4 and FIG. 5 in each case a schematic representation of the arrangement according to a first embodiment of the invention, FIG. 6 and FIG. 7 in each case a schematic representation of the arrangement according to a second embodiment of the invention, FIG. 8 a schematic representation of the arrangement according to the first embodiment of the invention in a first operating state, FIG. 9 a schematic representation of a holding element of a holding apparatus of an arrangement according to a third embodiment of the invention, FIG. 10 and FIG. 11 in each case a schematic representation of the arrangement according to a fourth embodiment of the invention, FIG. 12 and FIG. 13 in each case a schematic representation of the arrangement according to a fifth embodiment of the invention, FIG. 14 and FIG. 15 in each case a schematic representation of the arrangement according to a sixth embodiment of the invention, FIG. 16 a schematic representation of the arrangement according to a seventh embodiment of the invention, FIG. 17 a schematic representation of the arrangement according to an eighth embodiment of the invention, FIG. 18 a schematic representation of the arrangement according to a ninth embodiment of the invention, FIG. 19 and FIG. 20 in each case a schematic representation of the arrangement according to a tenth embodiment of the invention, FIG. 21 a schematic representation of the arrangement according to an eleventh embodiment of the invention, FIG. 22 a schematic representation of the arrangement according to a twelfth embodiment of the invention, FIG. 23 a flow diagram of a method for maintaining a component of a gantry of a computed tomography scanner according to a thirteenth embodiment of the invention.

FIG. 3 is a schematic representation of a gantry 20 of a computed tomography scanner 2, wherein the first rotating part R1 is connected to a crane apparatus TR1. The crane apparatus TR1 can be used to remove the first rotating part R1 of the gantry 20 from the stationary part S0 in the direction of the arrow parallel to the system axis AR. This typically requires one or more of the following measures:

removal of the patient-bearing apparatus 10 from the gantry 20, dismantling of lining parts and holders SC of the lining parts, dismantling of components arranged on the first rotating part R1.

Maintenance of the bearing assembly BG also typically requires dismantling of the second rotating part R2 and/or components arranged on the stationary part S0. Following maintenance of the bearing assembly BG, the dismantled components are re-assembled and/or adjusted and the patient-bearing apparatus 10 is adjusted relative to the gantry 20.

Figure 7:
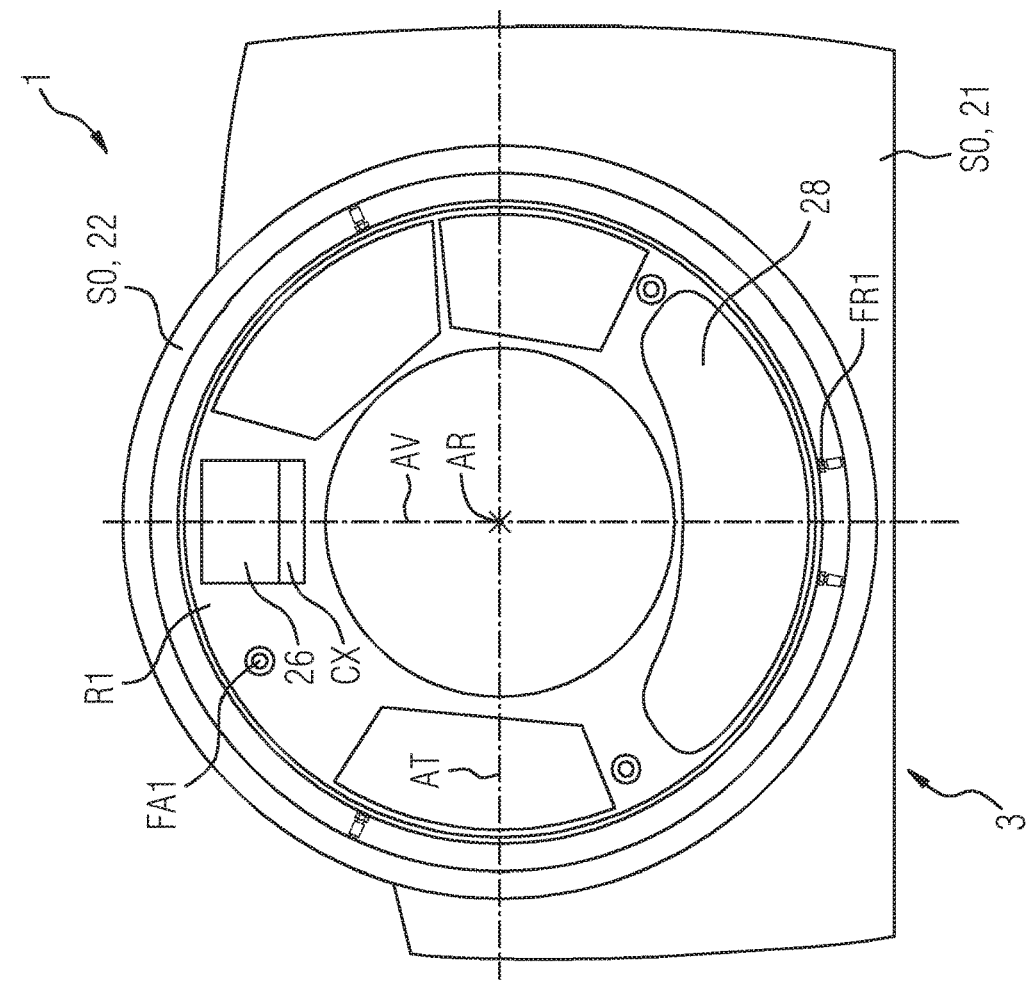
Figure 6:
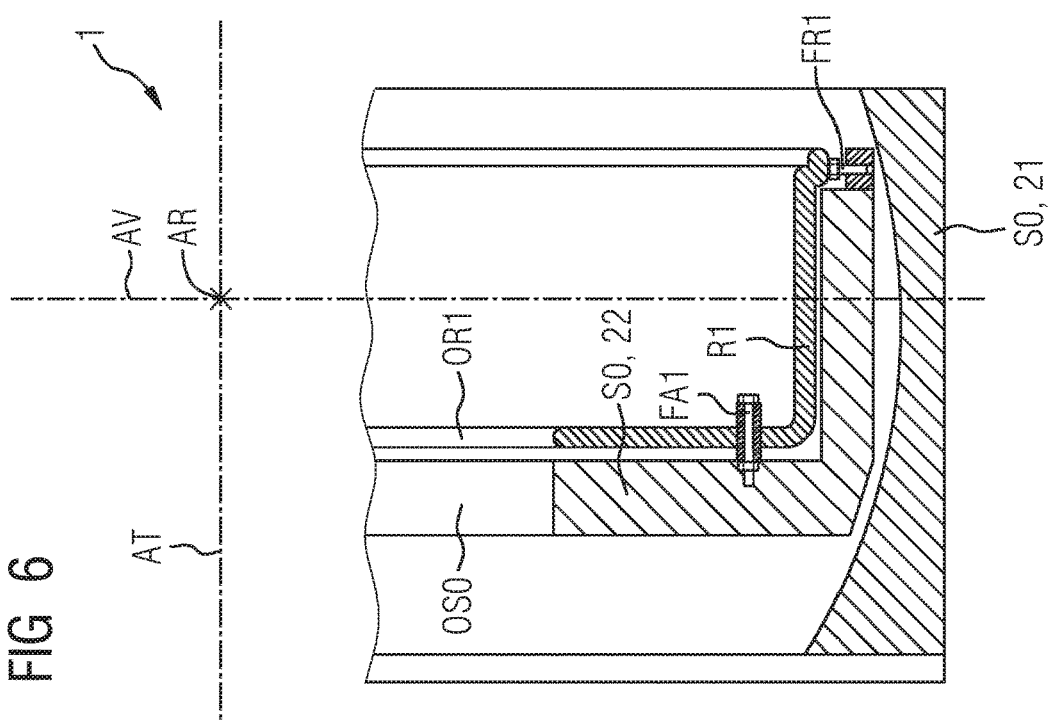

FIG. 4 and FIG. 5 in each case show a schematic representation of the arrangement 1 according to a first embodiment of the invention. FIG. 6 and FIG. 7 in each case show a schematic representation of the arrangement 1 according to a second embodiment of the invention. In FIGS. 4 to 7, the first rotating part R1 and the stationary part S0 are connected to one another via the holding apparatus 3 such that the first rotating part R1 is arranged in the holding position relative to the stationary part S0 independently of the bearing assembly BG. In the holding position, a central opening OR1 of the first rotating part R1 and a central opening OS0 of the stationary part S0 are arranged about the system axis AR. According to the second embodiment of the invention, the holding apparatus 3 comprises an axial part of the holding apparatus 3 with a plurality of holding elements in the form of screws FA1, which are arranged axially with respect to the system axis AR, in particular parallel to the system axis AR, and a radial part of the holding apparatus 3 with a plurality of holding elements in the form of screws FR1, which are arranged radially with respect to the system axis AR, in particular perpendicular to the system axis AR. The alignment of the screw FA1, FR1 can in particular be defined via the axis AF of the screw FA1, FR1 about which the screw FA1, FR1, rotates on a screw motion.

The first rotating part R1 is secured on the stationary part S0 via the axially arranged screws FA1 and the radial arranged screws FR1. The first rotating part R1 comprises a rotor-side connecting apparatus with a plurality of connecting elements in the form of threads for the screws FA1 and with a plurality of connecting elements in the form of bearing surfaces for the screws FR1. The bearing surfaces are formed by a surface of the first rotating part R1 facing the stationary part S0. Optionally, the bearing surfaces can, for example, be reinforced and/or marked. Alternatively and/or additionally to the connecting elements in the form of bearing surfaces for the screws FR1, the rotor-side connecting apparatus can comprise a plurality of connecting elements in the form of threads for the screws FR1. The stationary part S0 comprises a stator-side connecting apparatus with a plurality of connecting elements in the form of threads. The connecting elements are in each case embodied corresponding to the holding elements.

With the embodiments of the invention shown in FIGS. 4 to 7, it is provided that each of the screws FA1 is in each case connected to at least one thread of the rotor-side connecting apparatus and with at least one thread of the stator-side connecting apparatus and that each of the screws FR1 is in each case connected to at least one bearing surface of the rotor-side connecting apparatus and to at least one thread of the stator-side connecting apparatus. In an operating state of the arrangement 1, in which a connecting element is not connected to a holding element, the connecting element can for example, be at least partially covered via a cap plug. Alternatively and/or additionally to screws it is, for example, possible to use bolts, in particular threaded bolts. Alternatively and/or additionally to threads, it is, for example, possible to use recesses and/or bearing surfaces.

In FIGS. 4 to 7, the arrangement 1 is in each case shown in a second operating state, wherein, in the second operating state of the arrangement 1, the second rotating part R2 is arranged on the bearing assembly BG for common rotation with the first rotating part R1 such that the bearing assembly BG is located between the first rotating part R1 and the second rotating part R2 with respect to a direction parallel to the system axis AR. FIG. 8 is a schematic representation of the arrangement 1 according to the first embodiment of the invention in a first operating state, wherein the arrangement 1 comprises a support apparatus TBG, for example a gantry crane, for supporting the bearing assembly BG. The connection BC1 of the bearing assembly BG with the first rotating part R1, the connection BC2 of the bearing assembly BG with the second rotating part R2, the connection BC0 of the bearing assembly BG with the stationary part S0 is disconnected. The second rotating part R2 is removed from the bearing assembly BG and from the first rotating part R1 such that the bearing assembly BG and the interspace G01 are exposed on a side facing away from the first rotating part R1 with respect to a to a direction parallel the system axis AR, in particular are exposed such that the bearing assembly can be received in the interspace parallel to the system axis and/or removed from the interspace parallel to the system axis. The connection of the bearing assembly BG with the support apparatus TBG for supporting the bearing assembly BG is established. By way of the support apparatus TBG, the bearing assembly BG can be received in an interspace G01, which is embodied between the first rotating part R1 and the stationary part S0 to receive the bearing assembly BG, parallel to the system axis AR, and/or removed from the interspace G01 parallel to the system axis AR.

FIG. 9 is a schematic representation of a holding element of a holding apparatus 3 of an arrangement 1 according to a third embodiment of the invention, wherein the holding apparatus 3 comprises a holding element, which comprises a combination of a screw FA1, FR1 and a threaded sleeve TS. The threaded sleeve TS comprises an external thread. A washer W1 is arranged between the screw head of the screw FA1, FR1 and the threaded sleeve TS. The holding element is fixed relative to the first rotating part R1 by a lock nut N1. A washer W2 is arranged between the lock nut N1 and the first rotating part R1.

The holding element is connected to a connecting element of a rotor-side connecting apparatus in the form of a thread T1 and to a connecting element of a stator-side connecting apparatus in the form of a thread T0. The thread T0 can, for example, be formed by a threaded insert, in particular by a self-tapping threaded insert, and/or by a welding nut welded to the stationary part S0. Alternatively and/or additionally, the thread T0 can be directly cut into the stationary part S0. The thread T1 can, for example, be formed by a threaded insert, in particular by a self-tapping threaded insert, and/or by a welding nut welded to the first rotating part R1. Alternatively and/or additionally, the thread T1 can be directly cut into the first rotating part R1. One example of a self-tapping threaded insert is the Ensat®.

The connection shown in FIG. 9 forms a spacer and/or a tolerance compensation for a space between the first rotating part R1 and the stationary part S0. In particular, when FIG. 9 entails a screw FA1 arranged parallel to the system axis AR, the connection shown in FIG. 9 forms a spacer and/or a tolerance compensation for a space along the system axis AR between the first rotating part R1 and the stationary part S0.

FIG. 10 and FIG. 11 in each case show a schematic representation of the arrangement 1 according to a fourth embodiment of the invention, wherein the holding apparatus 3 comprises a plurality of holding elements in the form of threaded bolts F5, which can function as leveling feet. The rotor-side connecting apparatus in each case comprises connecting elements corresponding to the threaded bolt F5 in the form of threads. The stator-side connecting apparatus comprises in each case connecting elements in the form of bearing surfaces for the threaded bolt F5. The bearing surfaces are formed by a surface of the stationary part S0 facing the first rotating part R1. Optionally, the bearing surfaces can, for example, be reinforced and/or marked. For maintenance of the component of the gantry 20, in particular the bearing assembly BG, the thread can be fitted with the threaded bolt F5 and hence the first rotating part R1 arranged in the holding position relative to the stationary part S0 independently of the bearing assembly BG.

Figure 13:
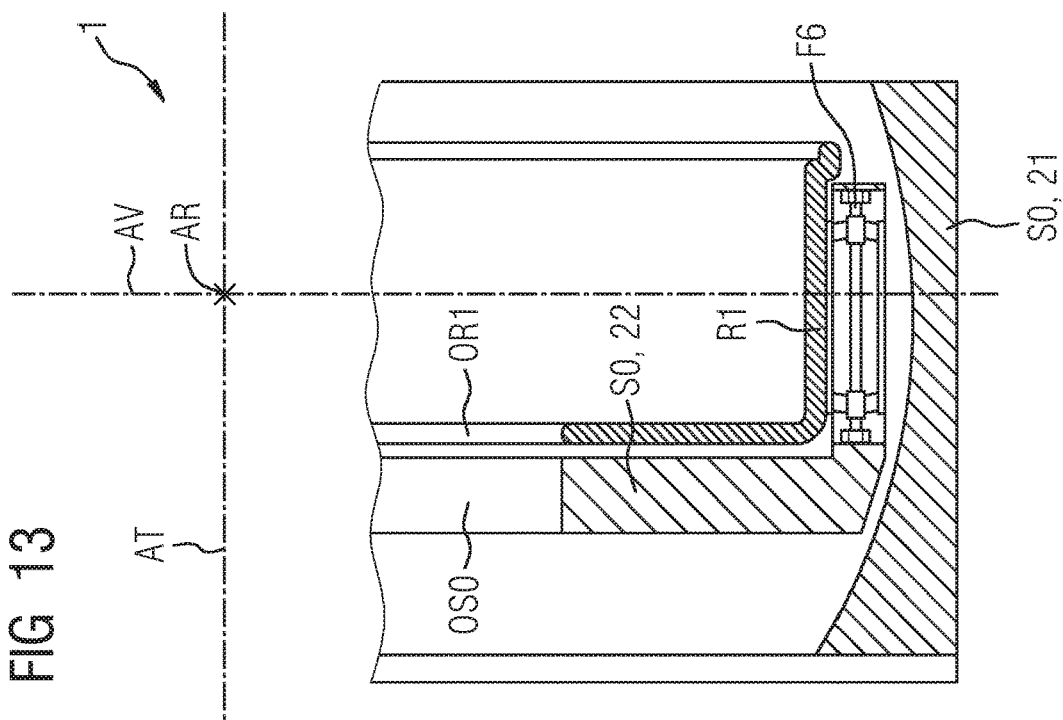
Figure 12:
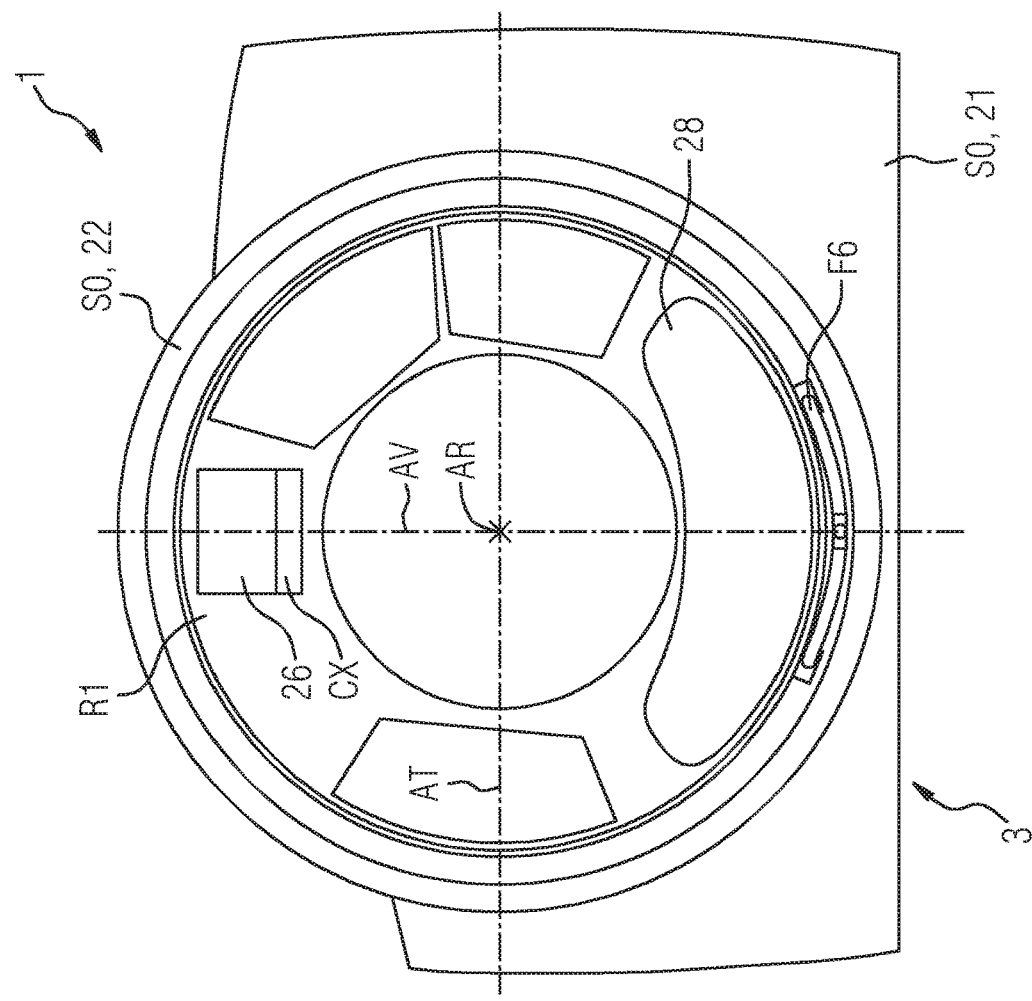

FIG. 12 and FIG. 13 in each case show a schematic representation of the arrangement 1 according to a fifth embodiment of the invention, wherein the holding apparatus 3 is a holding element in the shape of a jack F6, in particular a heavy-vehicle jack. The jack F6 can, for example, be installed in the gantry 20 between the first rotating part R1 and the stationary part S0 and/or introduced through an opening between the first rotating part R1 and the stationary part S0. If required, the jack F6 can be moved toward the first rotating part R1 via a jack-drive apparatus. The jack-drive apparatus can, for example, be connected to the jack F6 via a drive shaft for the transmission of a driving torque. The jack-drive apparatus can be arranged inside and/or outside the gantry 20 and/or operated by hand and/or via a motor.

Figure 15:
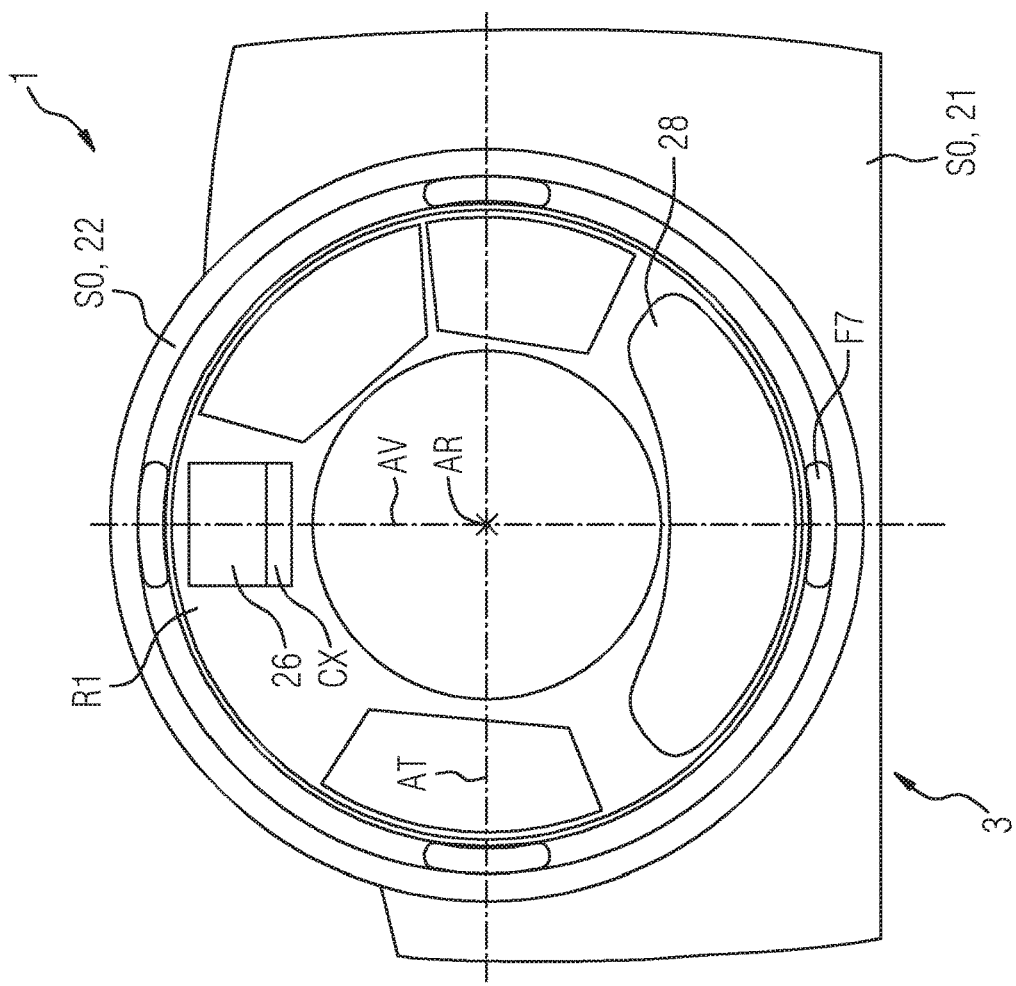
Figure 14:
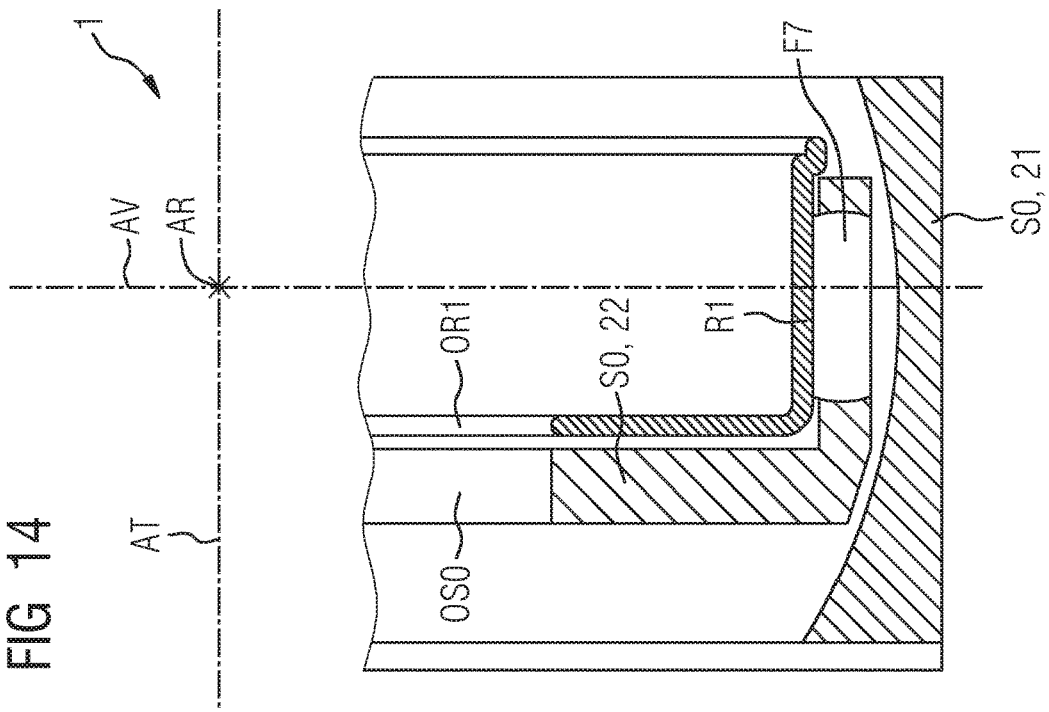

FIG. 14 and FIG. 15 are in each case schematic representations of the arrangement 1 according to a sixth embodiment of the invention, wherein the holding apparatus 3 comprises a plurality of holding elements in each case in the form of an aircushion F7. The aircushion F7 can, for example, be installed in the gantry 20 between the first rotating part R1 and the stationary part S0 and/or introduced through an opening between the first rotating part R1 and the stationary part S0. If required, the aircushion F7 can be moved toward the first rotating part R1 via an aircushion-ventilation apparatus. The aircushion-ventilation apparatus can, for example, be connected to the aircushion F7 via a compressed-air line for the transmission of compressed air. The aircushion-ventilation apparatus can be arranged inside and/or outside the gantry 20 and/or operated via a hand pump and/or via a motor pump and/or via a compressed-air supply unit.

FIG. 16 is a schematic representation of the arrangement 1 according to a seventh embodiment of the invention, wherein the holding apparatus 3 comprises a plurality of, in particular two, holding elements in each case in the form of an eccentric apparatus F8. The eccentric apparatus F8 comprises an eccentric bolt and a shaft for positioning the eccentric bolt, wherein the eccentric bolt is arranged on the shaft. In particular, the eccentric bolt is arranged eccentrically with respect to a shaft axis of the shaft on the shaft. The stator-side connecting apparatus comprises connecting elements in each case in the form of a holder for the eccentric apparatus F8. The rotor-side connecting apparatus comprises in each case connecting elements in the form of bearing surfaces for the eccentric bolt. The bearing surfaces are formed by a surface of the first rotating part R1 facing the stationary part S0. Optionally, the bearing surfaces can, for example, be reinforced and/or marked. If required, the eccentric bolt can be moved toward the first rotating part R1 via an eccentric apparatus-drive unit. The eccentric apparatus-drive unit can, for example, be connected to the shaft of the eccentric apparatus F8 via a drive shaft for the transmission of a driving torque. The eccentric apparatus-drive unit can be arranged inside and/or outside the gantry 20 and/or operated by hand and/or via a motor.

In particular, if the friction and/or the pressure between the eccentric bolt, on the one hand, and the rotor-side connecting elements, on the other hand, is sufficiently strong, the eccentric apparatuses are also able to prevent a rotational movement of the first rotating part R1 about the system axis AR relative to the stationary part S0. The eccentric apparatuses are arranged such that the eccentric bolt can absorb the weight force of the first rotating part R1. The two eccentric apparatuses are arranged symmetrically with respect to a vertical plane in which the system axis AR is located. Optionally, additionally to the plurality of eccentric apparatuses, the holding apparatus 3 can comprise an axial part of the holding apparatus 3, for example with a plurality of holding elements in the form of screws arranged axially with respect to the system axis AR, in particular parallel to the system axis AR. The axial part of the holding apparatus 3 can prevent a tilting movement of the first rotating part R1 about a horizontal axis perpendicular to the system axis AR, in particular if the connection BC1 of the bearing assembly BG to the first rotating part R1 is disconnected.

In particular, if an extension of the eccentric bolt along the system axis AR is sufficiently large, the eccentric apparatus F8 can prevent a tilting movement of the first rotating part R1 about a horizontal axis perpendicular to the system axis AR, in particular if the connection BC1 of the bearing assembly BG to the first rotating part R1 is disconnected.

FIG. 17 is a schematic representation of the arrangement 1 according to an eighth embodiment of the invention, wherein the holding apparatus 3 comprises a plurality of, in particular two, holding elements in each case in the form of a wedge apparatus F9. The wedge apparatus F9 comprises a wedge and a spindle, in particular a threaded spindle, for positioning the wedge, wherein the wedge is arranged on the spindle. The stator-side connecting apparatus comprises connecting elements in each case in the form of a holder for the wedge apparatus F9. The rotor-side connecting apparatus comprises in each case connecting elements in the form of bearing surfaces for the wedges. The bearing surfaces are formed by a surface of the first rotating part R1 facing the stationary part S0. Optionally, the bearing surfaces can, for example, be reinforced and/or marked. If required, the wedge can be moved toward the first rotating part R1 via a wedge-apparatus-drive unit. The wedge-apparatus-drive unit can, for example, be connected to the spindle of the wedge apparatus F9 via a drive shaft for the transmission of a driving torque. The wedge-apparatus-drive unit can be arranged inside and/or outside the gantry 20 and/or operated by hand and/or via a motor.

In particular, if the friction and/or the pressure between the wedges, on the one hand, and the rotor-side connecting elements, on the other hand, is sufficiently strong, the wedge apparatuses are also able to prevent a rotational movement of the first rotating part R1 about the system axis AR relative to the stationary part S0.

The wedge apparatuses are arranged such that the wedges are able to absorb the weight force of the first rotating part R1. The two wedge apparatuses are arranged symmetrically with respect to a vertical plane in which the system axis AR is located.

Optionally, additionally to the plurality of wedge apparatuses, the holding apparatus 3 can comprise an axial part of the holding apparatus 3, for example with a plurality of holding elements in the form of screws FA1 arranged axially with respect to the system axis AR, in particular parallel to the system axis AR. The axial part of the holding apparatus 3 can prevent a tilting movement of the first rotating part R1 about a horizontal axis perpendicular to the system axis AR, in particular if the connection BC1 of the bearing assembly BG to the first rotating part R1 is disconnected. In particular, if an extension of the wedges along the system axis AR is sufficiently large, the wedge apparatus F9 can prevent a tilting movement of the first rotating part R1 about a horizontal axis perpendicular to the system axis AR, in particular if the connection BC1 of the bearing assembly BG with the first rotating part R1 is disconnected.

Optionally, the arrangement can also comprise at least one component selected from the group consisting of the jack-drive apparatus, the aircushion-ventilation apparatus, the eccentric apparatus-drive unit, the wedge-apparatus-drive unit, the drive shaft for the transmission of a driving torque and a compressed-air line for the transmission of compressed air.

FIGS. 4 to 17 in each case show an operating state of the arrangement 1 according to the respective embodiment of the invention with which the holding apparatus 3 is located inside a region defined by the outer circumference of the gantry 20. FIGS. 18 to 21 in each case show an operating state of the arrangement 1 according to the respective embodiment of the invention with which the holding apparatus 3 is located outside or partially outside the region defined by the outer circumference of the gantry 20.

Figure 18:
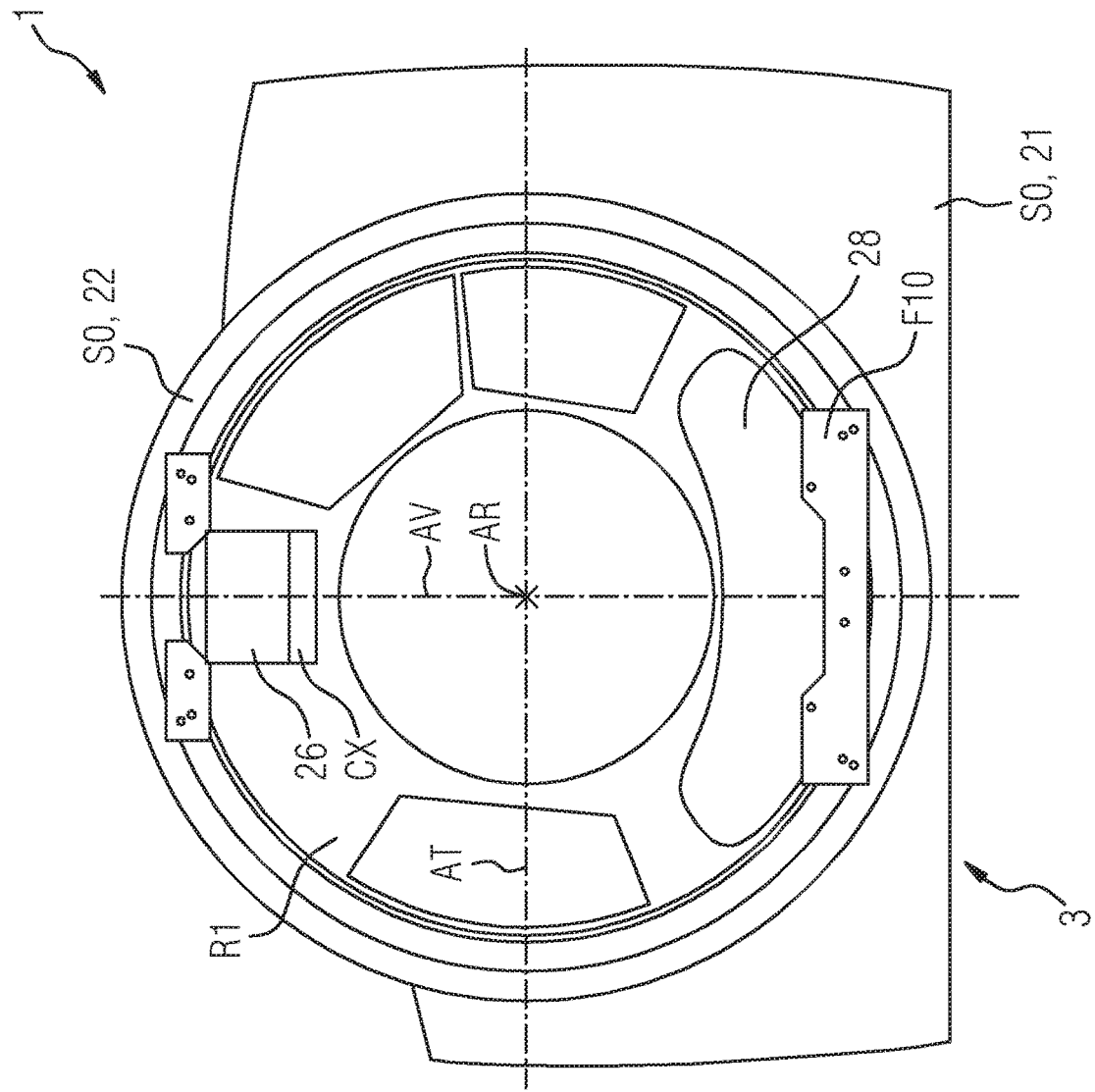

FIG. 18 is a schematic representation of the arrangement 1 according to a ninth embodiment of the invention, wherein the holding apparatus 3 comprises a plurality of holding elements in each case in the form of a holding segment F10. The holding apparatus 3 further comprises screwing apparatuses for connecting the holding segments to the first rotating part R1 and for connecting the holding segments to the stationary part S0. The stator-side connecting apparatus comprises connecting elements in each case in the form of a combination of a bearing surface for the holding segments and threads for the screwing apparatuses. The rotor-side connecting apparatus comprises connecting elements in each case in the form of a combination of a bearing surface for the holding segments and threads for the screwing apparatuses.

Figure 20:
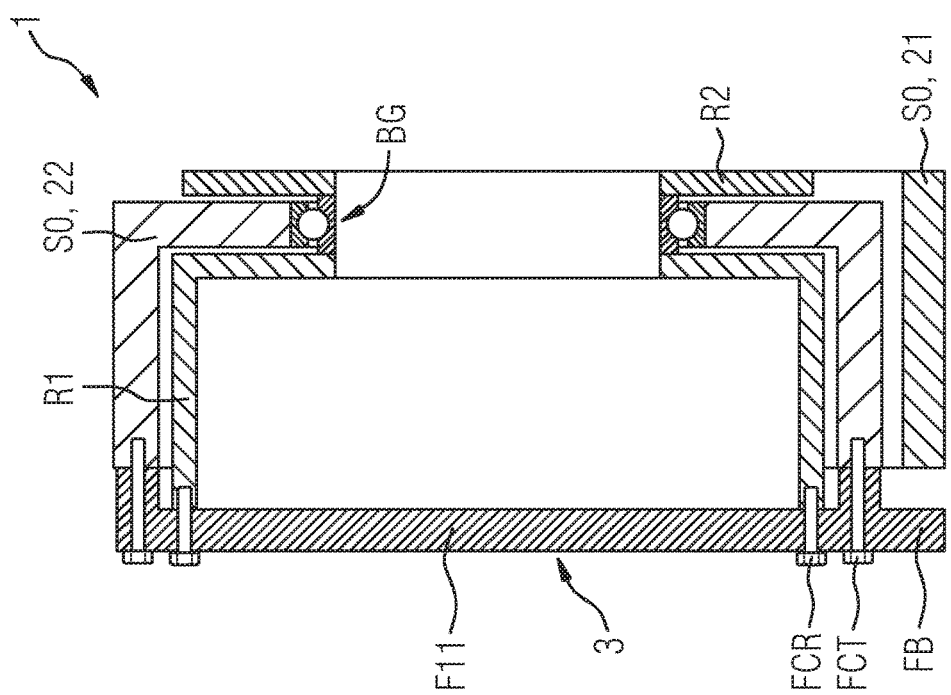
Figure 19:
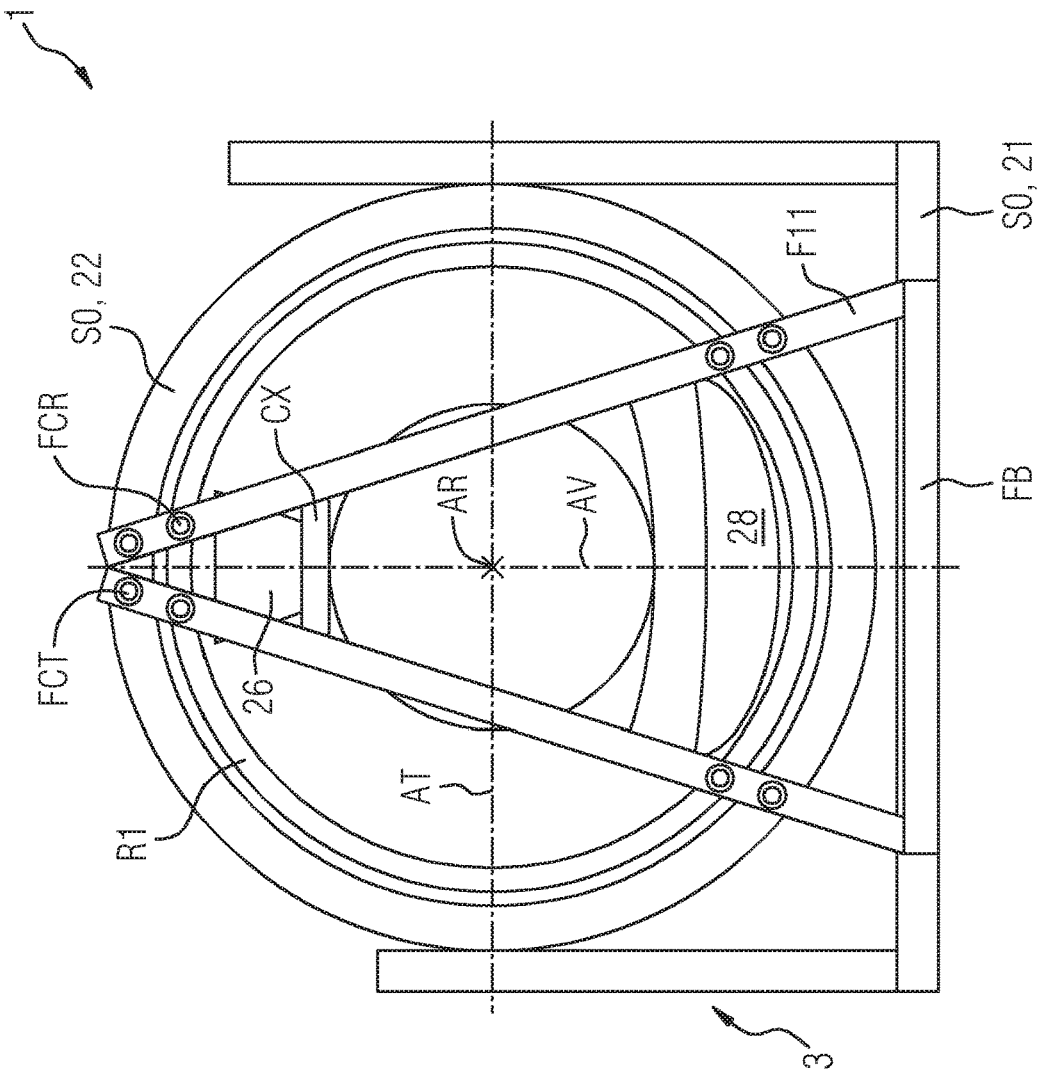

FIG. 19 and FIG. 20 both show a schematic representation of the arrangement 1 according to a tenth embodiment of the invention, wherein the holding apparatus 3 comprises a holding element in the form of the holding rack F11. FIG. 21 is a schematic representation of the arrangement 1 according to an eleventh embodiment of the invention, wherein the holding apparatus 3 comprises a holding element in the form of the holding rack F12. According to both the tenth embodiment of the invention and the eleventh embodiment of the invention, the holding apparatus 3 further comprises screwing apparatuses FCR for connecting the holding rack F11, F12 to the first rotating part R1 and screwing apparatuses FCT or FCS for connecting the holding rack F11, F12 to the stationary part S0. The stator-side connecting apparatus comprises connecting elements in each case in the form of a combination of a bearing surface for the holding rack F11, F12 and threads for the screwing apparatuses. The rotor-side connecting apparatus comprises connecting elements in each case in the form of a combination of a bearing surface for the holding rack F11, F12 and threads for the screwing apparatuses.

According to both the tenth embodiment of the invention and the eleventh embodiment of the invention, it is provided that the holding rack F11, F12 can be connected or is connected to the first rotating part R1 via the connection FCR and that the holding rack F11, F12 can be connected or is connected to the stationary part S0, in particular can be connected or is connected to the tilting frame 22, via the connection FCT. According to the eleventh embodiment of the invention, it is provided that the holding rack F12 can be connected or is connected to the stationary part S0, in particular to the supporting frame 21, via the connection FCS. Optionally, the holding rack F11, F12 can comprise a segment FB with which the holding rack F11, F12 can be supported on a support. The support can, for example, be a floor and/or a floor plate of the medical examination room. The supporting frame 21 can, for example, be arranged on the support fixed relative to the support.

FIG. 22 is a schematic representation of the arrangement 1 according to a twelfth embodiment of the invention, wherein the arrangement 1 comprises the computed tomography scanner 2. The computed tomography scanner 2 comprises the gantry 20, the tunnel-shaped opening 9, the patient-bearing apparatus 10 and the control apparatus 30. The gantry 20 comprises the stationary part S0 and the rotor 24. The stationary part S0 comprises the supporting frame 21 and the tilting frame 22. The rotor 24 comprises the first rotating part R1 and the second rotating part R2.

The first rotating part R1 is arranged in the bearing position on the stationary part S0 via the bearing assembly BG and can be rotated about the system axis AR via the bearing assembly BG. The patient can be introduced into the tunnel-shaped opening 9. The acquisition region 4 is located in the tunnel-shaped opening 9. A region of the patient 13 to be imaged can be positioned in the acquisition region 4 such that the radiation 27 from the radiation source 26 can travel to the region to be imaged and, following interaction with the region to be imaged, travel to the radiation detector 28. The patient-bearing apparatus 10 comprises the bearing table 11 and the transfer plate 12 for bearing the patient 13. The transfer plate 12 is arranged movably relative to the bearing table 11 on the bearing table 11 such that the longitudinal direction of the transfer plate 12 is parallel or substantially parallel to the system axis AR and that the transfer plate 12 can be introduced into the acquisition region 4 parallel or substantially parallel to the system axis AR. The supporting frame 21 is arranged fixed relative to the patient-bearing apparatus 10. The first rotating part R1 is located between the bearing assembly BG and the bearing table 11 in a direction parallel with respect to the system axis AR. The second rotating part R2 is located in a region of the room facing away from the bearing table 11 with respect to a vertical plane in which the tilt axis AT is located.

The computed tomography scanner 2 is embodied for the acquisition of imaging data based on an electromagnetic radiation 27. The computed tomography scanner 2 comprises an imaging-data acquisition unit. The imaging-data acquisition unit is a projection data-acquisition unit with the radiation source 26, for example an X-ray source, and the detector 28, for example an X-ray detector, in particular an energy-resolving X-ray detector. The radiation source 26 is arranged on the first rotating part R1 and embodied for the emission of radiation 27, for example X-rays, with radiation quanta 27. The detector 28 is arranged on the first rotating part R1 and embodied to detect radiation quanta 27. The radiation quanta 27 can travel from the radiation source 26 to the region of the patient 13 to be imaged and, following interaction with the region to be imaged, arrive at the detector 28. This enables the imaging-data acquisition unit to acquire imaging data of the region to be imaged in the form of projection data.

The control apparatus 30 is embodied to receive the imaging data acquired by the imaging-data acquisition unit. The control apparatus 30 comprises a computer 30 and is embodied to control the computed tomography scanner 2. The computer 30 comprises a storage mechanism 31 and a processor system. The control apparatus 30 comprises the image reconstruction mechanism 34. The image reconstruction mechanism 34 can be used to reconstruct a medical image dataset based on the imaging data. The computed tomography scanner 2 comprises an input apparatus 38 and an output apparatus 39 each of which are connected to the control apparatus 30. The input apparatus 38 is embodied to input control information, for example image reconstruction parameters and/or examination parameters. The output apparatus 39 is in particular embodied to output control information, images and/or tones.

FIG. 23 is a flow diagram of a method for maintaining a component of a gantry 20 of a computed tomography scanner 2 according to a thirteenth embodiment of the invention.

According to the thirteenth embodiment of the invention, it is provided that the first rotating part R1 of the gantry 20 and the stationary part S0 of the gantry 20 can be connected to one another via a bearing assembly BG such that the first rotating part R1 is arranged in a bearing position relative to the stationary part S0 and is mounted via the bearing assembly BG such that it can be rotated about a system axis AR and that the method comprises:

connecting CRS the first rotating part R1 and the stationary part S0 via a holding apparatus 3 such that the first rotating part R1 is arranged in a holding position relative to the stationary part S0 independently of the bearing assembly BG, wherein, in the holding position, a central opening OR1 of the first rotating part R1 and a central opening OS0 of the stationary part S0 are arranged about the system axis AR, and maintaining MC the component of the gantry 20.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An arrangement, comprising:
a stationary part of a gantry of a computed tomography scanner; and
a first rotating part of the gantry of the computed tomography scanner, the first rotating part and the stationary part being connectable to one another via a bearing assembly such that the first rotating part is arranged in a bearing position relative to the stationary part and is mounted via the bearing assembly to be rotatable about a system axis, the first rotating part and the stationary part being connectable to one another via a holding apparatus disposed within a space between the stationary part and the first rotating part such that
the first rotating part is arranged in a holding position relative to the stationary part independently of the bearing assembly, wherein, in both the bearing position and the holding position, a central opening of the first rotating part and a central opening of the stationary part are arranged about the system axis.

2. The arrangement of claim 1, wherein at least one of the holding position and the bearing position are arranged coaxially with respect to the system axis and the holding position and the bearing position coincide with respect to the position along the system axis.

3. The arrangement of claim 1, wherein the holding position and the bearing position are identical.

4. The arrangement of claim 1, wherein, in a first operating state of the arrangement, the first rotating part and the stationary part are connected to one another via the holding apparatus such that
the first rotating part is arranged in the holding position relative to the stationary part independently of the bearing assembly, and wherein, in the first operating state of the arrangement, at least one of
a connection between the bearing assembly and the first rotating part is at least one of establishable and disconnectable and
a connection between the bearing assembly and the stationary part is at least one of establishable and disconnectable.

5. The arrangement of claim 4, wherein, in the first operating state of the arrangement, a connection between the bearing assembly and a support apparatus for supporting the bearing assembly is at least one of establishable and disconnectable.

6. The arrangement of claim 4, wherein, in the first operating state of the arrangement, the bearing assembly is at least one of
receivable in an interspace embodied between the first rotating part and the stationary part to receive the bearing assembly and
removed from the interspace parallel to the system axis.

7. The arrangement of claim 1, further comprising:
at least one apparatus selected from the group consisting of the bearing assembly, the holding apparatus, a support apparatus for supporting the bearing assembly, the gantry, the computed tomography scanner and combinations thereof.

8. The arrangement of claim 1, wherein at least one of the stationary part comprises at least one of
a tilting frame of the gantry and
a supporting frame of the gantry and
the tilting frame is mounted relative to the supporting frame so as to be tiltable about a tilting axis.

9. The arrangement of claim 1, wherein the first rotating part is embodied to receive at least one of a radiation source and a radiation detector.

10. The arrangement of claim 1, further comprising:
a second rotating part of the gantry, wherein, in a second operating state of the arrangement, the second rotating part is arranged on at least one of the bearing assembly and the first rotating part for common rotation with the first rotating part such that the bearing assembly is located between the first rotating part and the second rotating part with respect to a direction parallel to the system axis, and wherein, in a first operating state of the arrangement, the second rotating part is located at a distance from at least one of the bearing assembly and the first rotating part such that at least one of the bearing assembly and an interspace is exposed on a side facing away from the first rotating part with respect to the direction parallel to the system axis.

11. The arrangement of claim 10, wherein the second rotating part is embodied to at least one of:
receive a rotor-side data-transfer unit of a data-transfer apparatus embodied to transfer data between the second rotating part and the stationary part and
receive a rotor-side power-transfer unit of a power-transfer apparatus embodied to transfer power between the second rotating part and the stationary part.

12. The arrangement of claim 1, wherein the holding apparatus is embodied to at least one of
form at least one of a disconnectable and positive connection with the first rotating part and
form at least one of a disconnectable and positive connection with the stationary part.

13. The arrangement of claim 1, wherein at least one of
the first rotating part comprises at least one rotor-side connecting apparatus, embodied to form at least one of a disconnectable and positive connection with the holding apparatus and
the stationary part comprises at least one stator-side connecting apparatus embodied to form at least one of a disconnectable and positive connection with the holding apparatus.

14. The arrangement of claim 1, wherein the holding apparatus comprises an axial part of the holding apparatus, and wherein the first rotating part and the stationary part are connectable to one another via the axial part of the holding apparatus such that the first rotating part is arranged in the holding position relative to the stationary part with respect to the position along the system axis independently of the bearing assembly.

15. The arrangement of claim 1, wherein the holding apparatus comprises a radial part of the holding apparatus, and wherein the first rotating part and the stationary part are connectable to one another via the radial part of the holding apparatus such that the first rotating part is arranged in the holding position relative to the stationary part with respect to the position along a direction perpendicular to the system axis independently of the bearing assembly.

16. The arrangement of claim 1, wherein the holding apparatus is a holding element selected from a holding-element group, or a plurality of holding elements each selected from the holding-element group, and wherein the holding-element group includes a screw, a threaded sleeve, a spacer sleeve, a bolt, a threaded bolt, an adjusting foot, a screwing apparatus, a supporting apparatus, a lifting apparatus, a jack, an aircushion, an eccentric apparatus, a wedge apparatus, a holding segment, a holding rack and combinations thereof.

17. A method for maintaining a component of a gantry of a computed tomography scanner, a first rotating part of the gantry and a stationary part of the gantry being connectable to one another via a bearing assembly such that the first rotating part is arranged in a bearing position relative to the stationary part and is mounted via the bearing assembly to be rotatable about a system axis, the method comprising:
directly connecting the first rotating part to the stationary part via a holding apparatus such that the first rotating part is secured in a holding position relative to the stationary part independently of the bearing assembly, wherein, in the holding position, a central opening of the first rotating part and a central opening of the stationary part are arranged about the system axis; and
maintaining the component of the gantry.

18. The method of claim 17, wherein the maintaining of the component of the gantry comprises at least one of repairing the component of the gantry and replacing the component of the gantry.

19. The method of claim 17, wherein at least one of
a connection between the bearing assembly and the first rotating part is at least one of establishable and disconnectable; and
a connection between the bearing assembly and the stationary part is at least one of establishable and disconnectable.

20. The method of claim 17, wherein a connection between the bearing assembly and a support apparatus for supporting the bearing assembly is at least one of establishable and disconnectable.

21. The method of claim 17, wherein the bearing assembly is at least one of
received in an interspace embodied between the first rotating part and the stationary part to receive the bearing assembly, and
removed from the interspace parallel to the system axis.

22. The method of claim 17, wherein a second rotating part is at least one of
located at a distance from at least one of the bearing assembly and the first rotating part such that at least one of the bearing assembly and an interspace is exposed on a side facing away from the first rotating part with respect to a direction parallel to the system axis, and
arranged on at least one of the bearing assembly and on the first rotating part for common rotation with the first rotating part.

23. The method of claim 17, wherein at least one of
the component of the gantry is the bearing assembly, and
the component of the gantry is arranged on at least one mechanism is arranged selected from the group consisting of the bearing assembly, the first rotating part, the stationary part and combinations thereof.

24. The method of claim 17, wherein a second rotating part is arranged on at least one of the bearing assembly and the first rotating part for common rotation with the first rotating part, and wherein the component of the gantry is at least one of the second rotating part and arranged on the second rotating part.

25. The method of claim 17, carried out an arrangement comprising:
a stationary part of a gantry of a computed tomography scanner; and
a first rotating part of the gantry of the computed tomography scanner, the first rotating part and the stationary part being connectable to one another via a bearing assembly such that the first rotating part is arranged in a bearing position relative to the stationary part and is mounted via the bearing assembly to be rotatable about a system axis, the first rotating part and the stationary part being connectable to one another via a holding apparatus such that the first rotating part is arranged in a holding position relative to the stationary part independently of the bearing assembly, wherein, in both the bearing position and the holding position, a central opening of the first rotating part and a central opening of the stationary part are arranged about the system axis.

26. The arrangement of claim 2, wherein the holding position and the bearing position are identical.

27. The arrangement of claim 2, wherein, in a first operating state of the arrangement, the first rotating part and the stationary part are connected to one another via the holding apparatus such that
the first rotating part is arranged in the holding position relative to the stationary part independently of the bearing assembly, and wherein, in the first operating state of the arrangement, at least one of
a connection between the bearing assembly and the first rotating part is at least one of establishable and disconnectable and
a connection between the bearing assembly and the stationary part is at least one of establishable and disconnectable.

28. The arrangement of claim 26, wherein, in a first operating state of the arrangement, the first rotating part and the stationary part are connected to one another via the holding apparatus such that
the first rotating part is arranged in the holding position relative to the stationary part independently of the bearing assembly, and wherein, in the first operating state of the arrangement, at least one of
a connection between the bearing assembly and the first rotating part is at least one of establishable and disconnectable and
a connection between the bearing assembly and the stationary part is at least one of establishable and disconnectable.

29. The arrangement of claim 5, wherein, in the first operating state of the arrangement, the bearing assembly is at least one of
receivable in an interspace embodied between the first rotating part and the stationary part to receive the bearing assembly and
removed from the interspace parallel to the system axis.

30. The method of claim 18, wherein at least one of
a connection between the bearing assembly and the first rotating part is at least one of establishable and disconnectable; and
a connection between the bearing assembly and the stationary part is at least one of establishable and disconnectable.

31. The method of claim 18, wherein a connection between the bearing assembly and a support apparatus for supporting the bearing assembly is at least one of establishable and disconnectable.

32. The method of claim 18, wherein the bearing assembly is at least one of
received in an interspace embodied between the first rotating part and the stationary part to receive the bearing assembly and
removed from the interspace parallel to the system axis.

33. An arrangement, comprising:
a stationary part of a gantry of a computed tomography scanner; and
a first rotating part of the gantry of the computed tomography scanner, the first rotating part and the stationary part being connectable to one another via a bearing assembly such that the first rotating part is arranged in a bearing position relative to the stationary part and is mounted via the bearing assembly to be rotatable about a system axis, the first rotating part and the stationary part being connectable to one another via a holding apparatus secured directly to each of the stationary part and the first rotating part such that
the first rotating part is arranged in a holding position relative to the stationary part independently of the bearing assembly, wherein, in both the bearing position and the holding position, a central opening of the first rotating part and a central opening of the stationary part are arranged about the system axis.

* * * * *